(12) United States Patent
Ishimori et al.

(10) Patent No.: US 9,532,940 B2
(45) Date of Patent: Jan. 3, 2017

(54) POROUS RESIN PARTICLES, METHOD FOR MANUFACTURING THE SAME, DISPERSION LIQUID, AND USE THEREOF

(75) Inventors: Fumitaka Ishimori, Koka (JP); Ryosuke Harada, Koka (JP)

(73) Assignee: Sekisui Plastics Co., Ltd., Osaka-shi (JP)

( * ) Notice: Subject to any disclaimer, the term of this patent is extended or adjusted under 35 U.S.C. 154(b) by 8 days.

(21) Appl. No.: 14/372,116

(22) PCT Filed: Jul. 31, 2012

(86) PCT No.: PCT/JP2012/069508
§ 371 (c)(1),
(2), (4) Date: Jul. 14, 2014

(87) PCT Pub. No.: WO2013/114653
PCT Pub. Date: Aug. 8, 2013

(65) Prior Publication Data
US 2015/0004127 A1  Jan. 1, 2015

(30) Foreign Application Priority Data

Jan. 31, 2012 (JP) .................. 2012-018302

(51) Int. Cl.
| | | |
|---|---|---|
| A61K 8/02 | (2006.01) | |
| A61Q 19/00 | (2006.01) | |
| C09D 201/00 | (2006.01) | |
| A61K 8/81 | (2006.01) | |
| C08F 220/26 | (2006.01) | |
| C09D 7/12 | (2006.01) | |
| C08F 2/24 | (2006.01) | |
| C08F 220/14 | (2006.01) | |
| C08F 222/10 | (2006.01) | |
| A61Q 1/12 | (2006.01) | |
| C08F 120/26 | (2006.01) | |
| C08K 5/05 | (2006.01) | |
| C08J 9/28 | (2006.01) | |
| C08J 9/16 | (2006.01) | |
| C09D 7/00 | (2006.01) | |
| C08J 3/12 | (2006.01) | |
| C08F 2/44 | (2006.01) | |

(52) U.S. Cl.
CPC ............ *A61K 8/8152* (2013.01); *A61K 8/022* (2013.01); *A61K 8/8182* (2013.01); *A61Q 1/12* (2013.01); *A61Q 19/00* (2013.01); *A61Q 19/007* (2013.01); *C08F 2/24* (2013.01); *C08F 2/44* (2013.01); *C08F 120/26* (2013.01); *C08F 220/14* (2013.01); *C08F 220/26* (2013.01); *C08F 222/1006* (2013.01); *C08J 3/124* (2013.01); *C08J 9/16* (2013.01); *C08J 9/286* (2013.01); *C08K 5/05* (2013.01); *C09D 7/005* (2013.01); *C09D 7/12* (2013.01); *C09D 201/00* (2013.01); *A61K 2800/54* (2013.01); *A61K 2800/594* (2013.01); *C08J 2201/0502* (2013.01); *C08J 2205/024* (2013.01); *C08J 2205/028* (2013.01); *C08J 2205/042* (2013.01); *C08J 2207/00* (2013.01); *C08J 2333/12* (2013.01); *C08J 2333/14* (2013.01); *C08J 2347/00* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 8,568,750 B2 * | 10/2013 | Harada ................ | C08F 2/22 424/401 |
| 2009/0137692 A1 | 5/2009 | Mori et al. | |
| 2012/0034281 A1 * | 2/2012 | Kaneko et al. ....... | A61K 8/0241 424/401 |

FOREIGN PATENT DOCUMENTS

| | | | |
|---|---|---|---|
| EP | 2055722 A1 | 5/2009 | |
| EP | 2754676 A1 | 7/2014 | |
| JP | 60-184004 A | 9/1985 | |
| JP | 63-092627 A | 4/1988 | |
| JP | 02-255704 A | 10/1990 | |
| JP | 04-051522 B2 | 8/1992 | |
| JP | 06-254373 A | 9/1994 | |
| JP | 2003-081738 A | 3/2003 | |
| JP | 2005-281470 A | 10/2005 | |
| JP | 2009-019100 A | 1/2009 | |
| JP | 2009-048184 A | 3/2009 | |
| JP | 2009-114269 A | 5/2009 | |
| JP | 2009-235273 A | 10/2009 | |
| JP | 2009-256625 A | 11/2009 | |
| JP | 2010-229229 A | 10/2010 | |
| JP | WO 2010113812 A1 * | 10/2010 | ............ C08F 2/22 |
| JP | WO 2010114125 A1 * | 10/2010 | .......... A61K 8/0241 |
| JP | 2011-094124 A | 5/2011 | |

OTHER PUBLICATIONS

International Search Report mailed Nov. 6, 2012, issued for PCT/JP2012/069508.
Supplementary European Search Report mailed Jul. 13, 2015, issued for the European Patent Application No. 12867125.2.

* cited by examiner

*Primary Examiner* — Abigail Fisher
(74) *Attorney, Agent, or Firm* — Locke Lord LLP

(57) ABSTRACT

Porous resin particles are disclosed that comprise a polymer of a monomer mixture. The monomer mixture includes: a mono(meth)acrylate-based monomer in an amount of 3 wt % to 40 wt % containing: an ethylenic unsaturated group only in a (meth)acrylic acid residue; and a hydroxyl group and at least either an ether group or an ester group in an alcohol residue; another monofunctional vinyl-based monomer in an amount of 10 wt % to 69 wt % containing a single ethylenic unsaturated group; and a polyfunctional vinyl-based monomer in an amount of 30 wt % to 70 wt % containing two or more ethylenic unsaturated groups.

19 Claims, 6 Drawing Sheets

POROUS RESIN PARTICLES, METHOD FOR MANUFACTURING THE SAME, DISPERSION LIQUID, AND USE THEREOF

TECHNICAL FIELD

The present invention relates in general to porous resin particles, a method for manufacturing the particles, a dispersion liquid, and their use, and in particular to porous resin particles with high water absorbance and high oil absorbance, a method for manufacturing the porous resin particles, a dispersion liquid containing the porous resin particles, and use of the porous resin particles (external preparations, coating materials, and light diffusion members containing the porous resin particles).

BACKGROUND ART

Conventional skin care products and other external preparations contain resin particles to fix skin flaws (to cover up spots, freckles, pores, etc.) by means of multiple light scattering effects and to improve spreading upon their application to the skin, as well as for various other purposes. Those resin particles are also blended with coating materials and light diffusion members to exploit multiple light scattering effects for matting or light diffusing purposes.

The external preparations containing the resin particles are in some cases required to have improved sweat and sebum absorbance so that they can render the skin smooth and silky when applied to the skin. Therefore, the resin particles used with the external preparations desirably have some water and oil absorbance.

For example, Patent Document 1, discloses a spherical polymer having an average particle diameter of 1 µm to 50 µm and an apparent specific gravity of 1.0 or less, each particle including one, two, or more spherical hollow tiny spaces inside it. The spherical polymer has some water and oil absorbance, absorbing 89.5 g to 110 g of water and 57.8 g to 82.3 g of oil (oleic acid) per every 100 g.

Patent Document 2 discloses porous spherical cellulose fine particles having an outer shell layer and a porous inner core having a porosity of 5% to 50%. The porous spherical cellulose fine particles have some water and oil absorbance, absorbing 170 g of water and 70 g of oil per every 100 g.

Patent Document 3 discloses porous spherical resin powder having particle diameters of 1 µm to 40 µm and an average particle diameter of 2 µm to 20 µm, the powder including pores of various sizes on the spherical surface with the mode pore diameter ranging from 5 angstroms to 160 angstroms (0.5 nm to 16 nm). The porous spherical resin powder has some water and oil absorbance, absorbing 74.6 g to 78.2 g of water and 81.4 g to 87.6 g of oil (oleic acid) per every 100 g.

Patent Document 4 discloses hollow flattened polymer fine particles having a shell wall made of an organic macromolecular compound. The hollow polymer fine particles become spherical upon absorbing a liquid substance and have some water and oil absorbance.

CITATION LIST

Patent Literature

Patent Document 1: Japanese Patent Application Publication, Tokukaisho, No. 60-184004
Patent Document 2: Japanese Patent Application Publication, Tokukaihei, No. 6-254373
Patent Document 3: Japanese Examined Patent Publication, Tokukouhei, No. 4-51522
Patent Document 4: Japanese Patent Application Publication, Tokukaihei, No. 2-255704

SUMMARY OF THE INVENTION

Problems to be Solved by the Invention

Although the particles disclosed in Patent Documents 1 to 3 have some water and oil absorbance, they are poor in either water absorbance or oil absorbance or in both. They do not show both high water absorbance and high oil absorbance.

In contrast, the particles disclosed in Patent Document 4 appear to show both high water absorbance and high oil absorbance because they have a shell wall made of an organic macromolecular compound that has a high degree of swelling (specifically, 1.5 to 10) for liquid substances (e.g., water and benzene). Each particle of Patent Document 4, however, has a single pore in it and is hollow. Therefore, the particles fall short of imparting sufficient multiple light scattering effects to external preparations, coating materials, or light diffusion members when compared with porous resin particles having a plurality of pores. Although the particles of Patent Document 4 become spherical upon absorbing a liquid substance, they change shape, becoming flattened, after discharging the liquid substance. For this reason, for example, a coating film formed by applying and then drying a coating material containing the particles disclosed in Patent Document 4 shows no multiple light scattering, hence no matting effects, because the particles have already discharged the liquid substance and become flattened. Furthermore, the coating film gives poor sense of touch for the same reason. The particles of Patent Document 4 are hardly compatible with the binder resin blended with the particles to produce the coating material and easily come off the coating film.

The present invention, conceived in view of these conventional problems, has an object of providing porous resin particles with high water absorbance and high oil absorbance, a method for manufacturing the porous resin particles, and a dispersion liquid, an external preparation, a coating material, and a light diffusion member prepared using the porous resin particles.

Solution to Problem

To achieve the object, porous resin particles in accordance with the present invention are porous resin particles of a polymer of a monomer mixture, the monomer mixture comprising: a mono(meth)acrylate-based monomer in an amount of 3 wt % to 40 wt % containing: an ethylenic unsaturated group only in a (meth)acrylic acid residue; and a hydroxyl group and at least either an ether group or an ester group in an alcohol residue; another monofunctional vinyl-based monomer in an amount of 10 wt % to 69 wt % containing a single ethylenic unsaturated group; and a polyfunctional vinyl-based monomer in an amount of 30 wt % to 70 wt % containing two or more ethylenic unsaturated groups.

The mono(meth)acrylate-based monomer contains a hydroxyl group, which is a hydrophilic group, and at least either an ether group or an ester group, which are both an hydrophilic group, in an alcohol residue. The mono(meth) acrylate-based monomer therefore has high affinity for at least a dispersion medium selected from the group consisting of water and alcohol (hereinafter, referred to as a "hydrophilic dispersion medium"). The porous resin particles in accordance with the present invention is a polymer of a monomer mixture containing the mono(meth)acrylate-based monomer, the other monofunctional vinyl-based monomer, and the polyfunctional vinyl-based monomer in respective, predetermined relative amounts. The porous resin particles in accordance with the present invention therefore contain structural units derived from the mono (meth)acrylate-based monomer that has high affinity for the hydrophilic dispersion medium in predetermined relative amounts. The porous resin particles in accordance with the present invention hence have high affinity for the hydrophilic dispersion medium. In addition, the porous resin particles in accordance with the present invention exhibit high water absorbance and high oil absorbance due to their porous structure as well as its their affinity for the hydrophilic dispersion medium, and when blended in external preparations, coating materials, or light diffusion members, impart high multiple light scattering effects to the external preparations, coating materials, and light diffusion members. Furthermore, the porous resin particles in accordance with the present invention have superior redispersibility in the hydrophilic dispersion medium due to their high affinity for the hydrophilic dispersion medium. Note that throughout the present specification, "(meth)acrylic" means acrylic or methacrylic, and "(meth)acrylate" means acrylate or methacrylate.

To solve the problems, other porous resin particles in accordance with the present invention have a water absorption value of 140 ml to 400 ml per 100 g of the porous resin particles, an oil absorption value of 100 ml to 400 ml per 100 g of the porous resin particles, and pore diameter of 4 nm to 20 nm. Note that throughout the present specification, the "water absorption value" refers to the water absorption value measured by the method of measuring a water absorption value that will be detailed later in the examples of the invention, and the "oil absorption value" refers to the oil absorption value measured by the method of measuring an oil absorption value that will be detailed later in the examples of the invention.

The other porous resin particles in accordance with the present invention have a water absorption value of 140 ml to 400 ml per 100 g of the porous resin particles and oil absorption value of 100 ml to 400 ml per 100 g of the porous resin particles, exhibiting both high water absorbance and high oil absorbance. In addition, the other porous resin particles have pore diameter of from 4 nm to 20 nm, and when blended in external preparations, coating materials, or light diffusion members, impart high multiple light scattering effects to the external preparations, coating materials, and light diffusion member.

A method for manufacturing porous resin particles in accordance with the present invention includes the step of suspension-polymerizing a monomer mixture in the presence of a non-polymerizable organic solvent as a pore-forming agent, an anionic surfactant, and a zwitterionic surfactant, wherein the monomer mixture comprises: a mono(meth)acrylate-based monomer in an amount of 3 wt % to 40 wt % containing: an ethylenic unsaturated group only in a (meth)acrylic acid residue; and a hydroxyl group and at least either an ether group or an ester group in an alcohol residue; another monofunctional vinyl-based monomer in an amount of 10 wt % to 69 wt % containing a single ethylenic unsaturated group; and a polyfunctional vinyl-based monomer in an amount of 30 wt % to 70 wt % containing two or more ethylenic unsaturated groups, wherein in the step, the pore-forming agent is used in from 50 parts by weight to 300 parts by weight per 100 parts by weight of the monomer mixture.

According to the manufacturing method in accordance with the present invention, the monomer mixture is suspension-polymerized in the presence of a non-polymerizable organic solvent as a pore-forming agent, an anionic surfactant, and a zwitterionic surfactant. The method is therefore capable of manufacturing porous resin particles that exhibit high water absorbance and high oil absorbance and when blended in an external preparation, coating material, or light diffusion member, impart high multiple light scattering effects to the external preparation, coating material, and light diffusion member. Furthermore, the manufacturing method in accordance with the present invention uses a monomer mixture containing the mono(meth)acrylate-based monomer, the other monofunctional vinyl-based monomer, and the polyfunctional vinyl-based monomer in respective, predetermined relative amounts. The porous resin particles obtained by the method therefore contain structural units derived from the mono(meth)acrylate-based monomer that has high affinity for the hydrophilic dispersion medium in predetermined relative amounts. The porous resin particles therefore have high affinity for the hydrophilic dispersion medium.

A dispersion liquid in accordance with the present invention contains: the porous resin particles in accordance with the present invention; and at least one dispersion medium selected from the group consisting of water and alcohol.

The dispersion liquid in accordance with the present invention exhibits high water absorbance and high oil absorbance because it contains the porous resin particles in accordance with the present invention which exhibit high water absorbance and high oil absorbance.

An external preparation in accordance with the present invention contains the porous resin particles in accordance with the present invention.

The external preparation in accordance with the present invention exhibits high water absorbance and high oil absorbance because it contains the porous resin particles in accordance with the present invention which exhibit high water absorbance and high oil absorbance.

A coating material in accordance with the present invention contains the porous resin particles in accordance with the present invention.

The coating material in accordance with the present invention exhibits high water absorbance and high oil absorbance because it contains the porous resin particles in accordance with the present invention which exhibit high water absorbance and high oil absorbance.

A light diffusion member in accordance with the present invention contains the porous resin particles in accordance with the present invention.

The light diffusion member in accordance with the present invention exhibits excellent light diffusibility because it contains the porous resin particles in accordance with the present invention.

Advantageous Effects of the Invention

The present invention provides porous resin particles with high water absorbance and high oil absorbance, a method for manufacturing the porous resin particles, and a dispersion liquid, an external preparation, a coating material, and a light diffusion member prepared using the porous resin particles.

DESCRIPTION OF EMBODIMENTS

Figure 1:
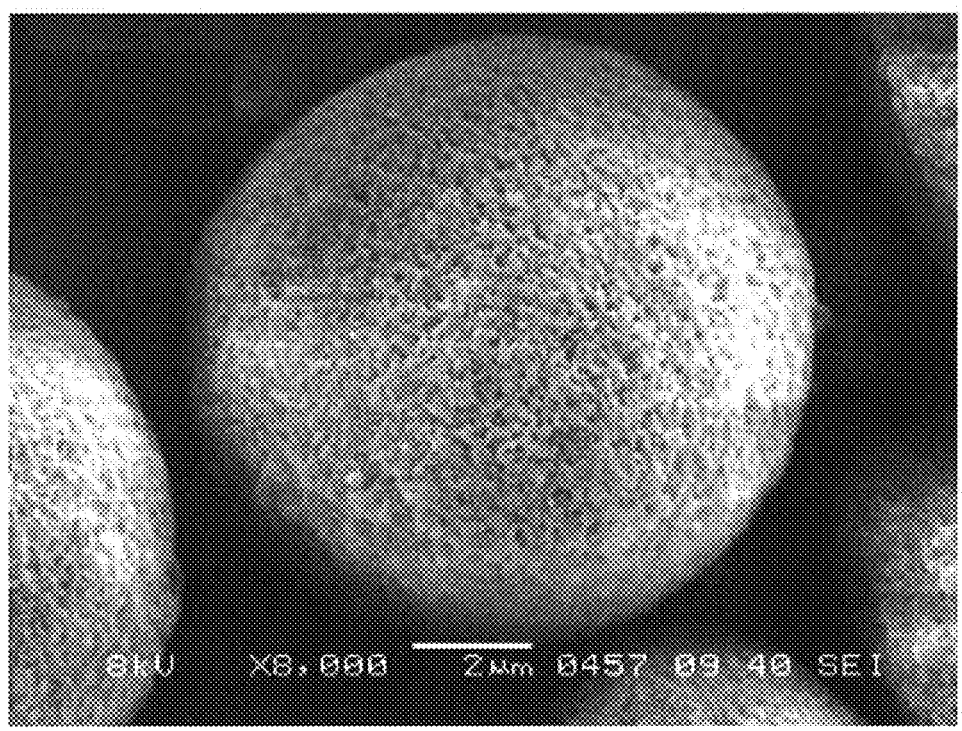
FIG. 1 is a scanning electron microscope (SEM) image of porous resin particles in accordance with example 3 of the present invention.

The following will describe the present invention in detail.

Porous Resin Particles

Porous resin particles in accordance with the present invention are porous resin particles of a polymer of a monomer mixture. The monomer mixture includes: a mono(meth)acrylate-based monomer in an amount of 3 wt % to 40 wt % containing, in an alcohol residue, a hydroxyl group and at least either an ether group or an ester group, said mono(meth)acrylate-based monomer containing an ethylenic unsaturated group only in a (meth)acrylic acid residue; another monofunctional vinyl-based monomer in an amount of 10 wt % to 69 wt % containing a single ethylenic unsaturated group; and a polyfunctional vinyl-based monomer in an amount of 30 wt % to 70 wt % containing two or more ethylenic unsaturated groups.

These porous resin particles in accordance with the present invention are spherical and have excellent water and oil absorbance. For example, the porous resin particles in accordance with the present invention have a water absorption value of 140 ml to 400 ml per 100 g of the particles and an oil absorption value of 100 ml to 400 ml per 100 g of the particles.

The quantification and qualitative analysis of the structural unit derived from a monomer for the porous resin particles in accordance with the present invention may be checked by gas chromatography, liquid chromatography, infrared (IR) spectroscopy, nuclear magnetic resonance (NMR) spectroscopy, or any other publicly known analytical method. The weight ratio of monomers in the monomer mixture is substantially equal to the weight ratio of the structural units derived from those monomers in the porous resin particles in accordance with the present invention.

Mono(meth)acrylate-Based Monomer

The porous resin particles in accordance with the present invention contain structural units derived from a mono(meth)acrylate-based monomer.

The mono(meth)acrylate-based monomer is an ester formed by a (meth)acrylic acid residue and an alcohol residue and contains: an ethylenic unsaturated group only in a (meth)acrylic acid residue; and a hydroxyl group and at least either an ether group or an ester group in an alcohol residue. The mono(meth)acrylate-based monomer may be any publicly known mono(meth)acrylate-based monomer containing: an ethylenic unsaturated group only in a (meth)acrylic acid residue; and a hydroxyl group and at least either an ether group or an ester group in an alcohol residue as long as that monomer does not affect the water and oil absorbance of the porous resin particles. The mono(meth)acrylate-based monomer is preferably a mono(meth)acrylate ester (aliphatic mono(meth)acrylate-based monomer) containing an aliphatic hydrocarbon group as a hydrocarbon group in its alcohol residue. The ether group may be, for example, a group derived from ethylene glycol (an oxyethylenic group having an oxygen atom bonded to a carbon atom) or a group derived from propylene glycol (an oxypropylene group having an oxygen atom bonded to a carbon atom). The ester group may be a group derived from lactone (an oxycarbonyl alkylene group having an oxygen atom bonded to a carbon atom).

From that viewpoint, the mono(meth)acrylate-based monomer is preferably, in particular, a compound of either general formula (1) or general formula (2):

  (1)

where R is either H or $CH_3$, l is from 0 to 50, m is from 0 to 50, and l+m>1, and

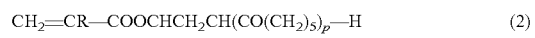  (2)

where R is either H or $CH_3$, and p is from 1 to 50.

In the compound of general formula (1), if l is greater than 50, the porous resin particles have a lower porosity, hence possibly leading to insufficient water and oil absorbance, and have less polymerization stability, possibly resulting in coalescence and poor redispersibility of the porous resin particles. In the compound of general formula (1), if m is greater than 50, the porous resin particles have a lower porosity, hence possibly leading to insufficient water and oil absorbance, and have less polymerization stability, possibly resulting in coalescence and poor redispersibility of the porous resin particles. If l+m is less than or equal to 1, the compound of general formula (1) contains no ether bonds in its alcohol residues. Preferably, l and m range from 1 to 30. More preferably, l and m range from 1 to 7. If l and m are within either of those ranges, the porous resin particles have a sufficient porosity, hence leading to further improvement of water and oil absorbance, and have reduced chances of coalescence and further improved redispersibility. In the compound of general formula (1), the oxyethylenic groups and the oxypropylene groups in the compound where l and m are both greater than 1 may appear in blocks (i.e., the same kind of groups may appear next to each other) or in any other sequence as long as that sequence does not affect desirable physical properties.

In the compound of general formula (2), if p is greater than 50, the porous resin particles have a lower porosity, hence possibly leading to insufficient water and oil absorbance, and have less polymerization stability, possibly resulting in coalescence and poor redispersibility of the porous resin particles. Preferably, p ranges from 1 to 30. If p is within that range, the porous resin particles have a sufficient porosity, hence leading to further improvement of water and oil absorbance, and have reduced chances of coalescence and further improved redispersibility.

Either a compound of general formula (1) or a compound of general formula (2) may be used alone. Alternatively, two or more of them may be used together.

The mono(meth)acrylate-based monomer may be a commercial product. An exemplary commercial product of the mono(meth)acrylate-based monomer of general formula (1) is the Blemmer® series manufactured by NOF Corporation. Of the Blemmer® series, Blemmer® 50 PEP-300 (a mixture of compounds of general formula (1) where R is $CH_3$, l is about 3.5 on average, and m is about 2.5 on average), which is a poly(ethylene glycol-propylene glycol) monomethacrylate, and Blemmer® 70 PEP-350B (a mixture of compounds of general formula (1) where R is $CH_3$, l is about 5 on average, and m is about 2 on average), which is a poly (ethylene glycol-propylene glycol) monomethacrylate, are suitable to the present invention. Any one of these commercial products may be used alone. Alternatively, two or more of them may be mixed for use.

An exemplary commercial product of the mono(meth) acrylate-based monomer of general formula (2) is the Placcel® FM series manufactured by Daicel Corporation. Of the Placcel® FM series, Placcel® FM2D (a compound of general formula (2), where R is $CH_3$, and p is 2) and Placcel® FM3 (a compound of general formula (2), where R is $CH_3$, and p is 3) are suitable to the present invention. Any one of these commercial products may be used alone. Alternatively, two or more of them may be mixed for use.

The mono(meth)acrylate-based monomer is used in an amount of from 3 wt % to 40 wt % as based on the total amount of the monomer mixture. If the mono(meth)acrylate-based monomer is used in an amount of less than 3 wt % as based on the total amount of the monomer mixture, the porous resin particles have less affinity for a hydrophilic dispersion medium, hence possibly resulting in a lower water absorption value, and may fail to exhibit sufficient redispersibility in the hydrophilic dispersion medium. Meanwhile, if the mono(meth)acrylate-based monomer is used in an amount of more than 40 wt % as based on the total amount of the monomer mixture, the porous resin particles have a lower porosity, hence possibly resulting in a lower water absorption value and a lower oil absorption value, and may have insufficient redispersibility in the hydrophilic dispersion medium. The mono(meth)acrylate-based monomer is used in an amount of more preferably from 5 wt % to 30 wt %, and even more preferably from 10 wt % to 20 wt %, as based on the total amount of the monomer mixture. These ranges further improve the water and oil absorbance of the porous resin particles and the redispersibility of the porous resin particles in the hydrophilic dispersion medium.

Other Monofunctional Vinyl-Based Monomer

The porous resin particles in accordance with the present invention contain structural units derived from another monofunctional vinyl-based monomer containing a single ethylenic unsaturated group. The other monofunctional vinyl-based monomer may be any publicly known monofunctional vinyl-based monomer, except for the mono(meth) acrylate-based monomer, containing a single ethylenic unsaturated group as long as that monomer does not affect the water and oil absorbance of the porous resin particles in accordance with the present invention.

Examples of the other monofunctional vinyl-based monomer include (meth)acrylates, alkyl(meth)acrylate-based monomers, 2-hydroxyethyl methacrylate, 2-methoxyethyl methacrylate, glycidyl methacrylate, tetrahydrofurfuryl methacrylate, diethylaminoethyl methacrylate, trifluoroethyl methacrylate, heptadecafluorodecyl methacrylate, styrene-based monomers, and vinyl acetate. Of these other monofunctional vinyl-based monomers, alkyl(meth)acrylate-based monomers have excellent effects in improving the redispersibility of the porous resin particles. Therefore, the other monofunctional vinyl-based monomer preferably contains an alkyl(meth)acrylate-based monomer.

The alkyl group in the alkyl(meth)acrylate-based monomer may be straight chained or branched. Examples of the alkyl(meth)acrylate-based monomer include alkyl acrylates, such as methyl acrylate, ethyl acrylate, n-butyl acrylate, isobutyl acrylate, and 2-ethyl hexyl acrylate; and alkyl methacrylates, such as n-butyl methacrylate, 2-ethyl hexyl methacrylate, methyl methacrylate, ethyl methacrylate, isobutyl methacrylate, cyclohexyl methacrylate, benzyl methacrylate, and isobornyl methacrylate. The alkyl group in the alkyl(meth)acrylate-based monomer is preferably a $C_1$-$C_8$ alkyl group and more preferably a $C_1$-$C_4$ alkyl group. If the alkyl group in the alkyl(meth)acrylate-based monomer contains 1 to 8 carbon atoms, the porous resin particles have more affinity for the hydrophilic dispersion medium, hence exhibiting improved water absorbance and redispersibility in the hydrophilic dispersion medium. The other monofunctional vinyl-based monomer preferably contains methyl methacrylate to obtain porous resin particles that have superior water and oil absorbance and superior redispersibility in the hydrophilic dispersion medium.

Examples of the styrene-based monomer include styrene, p-methyl styrene, and α-methyl styrene.

Any one of these other monofunctional vinyl-based monomers may be used alone. Alternatively, two or more of them may be combined for use.

The other monofunctional vinyl-based monomer is used in an amount of from 10 wt % to 69 wt % as based on the total amount of the monomer mixture. If the other monofunctional vinyl-based monomer is used in an amount of less than 10 wt % as based on the total amount of the monomer mixture, the polymerization reaction of the monomer mixture does not sufficiently proceed, which likely leaves unreacted monomer. Meanwhile, if the other monofunctional vinyl-based monomer is used in an amount of more than 69 wt % as based on the total amount of the monomer mixture, the porous resin particles have a lower porosity, hence possibly leading to insufficient water and oil absorbance. The other monofunctional vinyl-based monomer is used in an amount of more preferably from 10 wt % to 50 wt %, and even more preferably from 10 wt % to 30 wt %, as based on the total amount of the monomer mixture. These ranges further improve the water absorbance and the oil absorbance.

Polyfunctional Vinyl-Based Monomer

The porous resin particles in accordance with the present invention contain structural units derived from a polyfunctional vinyl-based monomer containing two or more ethylenic unsaturated groups. The polyfunctional vinyl-based monomer may be any publicly known polyfunctional vinyl-based monomer containing two or more ethylenic unsaturated groups as long as that monomer does not affect the water and oil absorbance of the porous resin particles in accordance with the present invention.

Examples of the polyfunctional vinyl-based monomer include polyfunctional (meth)acrylate-based monomers that contain two or more ethylenic unsaturated groups and aromatic divinyl-based monomers.

Examples of the polyfunctional (meth)acrylate-based monomer include ethylene glycol di(meth)acrylate, diethylene glycol di(meth)acrylate, triethylene glycol di(meth)acrylate, tetraethylene glycol di(meth)acrylate, nonaethylene glycol di(meth)acrylate, tetradecaethylene glycol di(meth)acrylate, decaethylene glycol di(meth)acrylate, pentadecaethylene glycol di(meth)acrylate, 1,3-butylene glycol di(meth)acrylate, 1,4-butanediol di(meth)acrylate, 1,6-hexanediol di(meth)acrylate, glycerin di(meth)acrylate, trimethylolpropane tri(meth)acrylate, pentaerythritol tetra (meth)acrylate, phthalate diethylene glycol di(meth)acrylate, caprolactone-modified dipentaerythritol hexa(meth) acrylate, caprolactone-modified neopentyl glycol hydroxypivalate di(meth)acrylate, polyester acrylate, and urethane acrylate.

Examples of the aromatic divinyl-based monomer include divinyl benzene, divinyl naphthalene, and their derivatives.

Any one of these polyfunctional vinyl-based monomers may be used alone. Alternatively, two or more of them may be combined for use. Of the polyfunctional vinyl-based monomers, ethylene glycol di(meth)acrylate is excellent in improving the water and oil absorbance of the porous resin particles. Therefore, the polyfunctional vinyl-based monomer preferably contains ethylene glycol di(meth)acrylate.

The polyfunctional vinyl-based monomer is used in an amount of from 30 wt % to 70 wt % as based on the total amount of the monomer mixture. If the polyfunctional vinyl-based monomer is used in an amount of less than 30 wt % as based on the total amount of the monomer mixture, the porous resin particles have a lower porosity, hence possibly leading to insufficient water and oil absorbance. Meanwhile, if the polyfunctional vinyl-based monomer is used in an amount of more than 70 wt % as based on the total amount of the monomer mixture, the use of the extra amount does not produce rewarding effects, and the polymerization reaction of the monomer mixture does not sufficiently proceed, which likely leaves unreacted monomer. The polyfunctional vinyl-based monomer is used in an amount of more preferably from 40 wt % to 70 wt %, and even more preferably from 50 wt % to 70 wt %, as based on the total amount of the monomer mixture. These ranges further improve the water absorbance and the oil absorbance.

The porous resin particles in accordance with the present invention have a plurality of pores (in other words, the particles are porous) with pore diameter of preferably from 4 nm to 20 nm and more preferably from 4 nm to 15 nm. If the pore diameter is less than 4 nm, the water and oil absorbance may be insufficient. If the pore diameter is more than 20 nm, the multiple light scattering effects may be insufficient. In the present invention, the pore diameter refers to the pore diameter (average pore diameter) obtained by the BJH method from nitrogen adsorption isotherm, for example, the pore diameter (average pore diameter) obtained from measurements by a pore diameter measuring method which will be described later in detail in the examples of the invention.

The porous resin particles in accordance with the present invention have a specific surface area of preferably from 3 $m^2/g$ to 300 $m^2/g$, more preferably from 5 $m^2/g$ to 300 $m^2/g$, and even more preferably from 5 $m^2/g$ to 200 $m^2/g$. If the porous resin particles have a specific surface area of less than 3 $m^2/g$, the water and oil absorbance and the multiple light scattering effects may be insufficient. Meanwhile, if the porous resin particles have a specific surface area of more than 300 $m^2/g$, the porous resin particles are no longer spherical; if such porous resin particles are blended in an external preparation, the external preparation may show less spreading and slippage when applied to the skin; if the porous resin particles are blended in a coating material, the coating film formed from the coating material may likely have bumps (projections).

The specific surface area refers to the surface area per unit weight and in the present invention refers to the specific surface area obtained by the BET method ($N_2$). The method of measuring the specific surface area by the BET method ($N_2$) will be described in the examples of the invention.

The porous resin particles in accordance with the present invention have a volume-average particle diameter of preferably from 4 µm to 40 µm and more preferably from 4 µm to 20 µm. If the volume-average particle diameter is within these ranges, the porous resin particles in accordance with the present invention unfailingly have sufficient surface areas, hence unfailingly exhibiting sufficient water and oil absorbance and sufficient redispersibility in the hydrophilic dispersion medium.

The porous resin particles in accordance with the present invention have a coefficient of variation (CV) of particle diameters of preferably less than or equal to 50% and more preferably less than or equal to 40%. If the particle diameters have a coefficient of variation in these ranges, the external preparation (e.g., cosmetic material) in which the porous resin particles are blended exhibits improved spreading and slippage.

Method for Manufacturing Porous Resin Particles

The porous resin particles in accordance with the present invention may be manufactured by a method for manufacturing porous resin particles including the step of suspension-polymerizing a monomer mixture in the presence of a non-polymerizable organic solvent as a pore-forming agent, an anionic surfactant, and a zwitterionic surfactant, wherein in the step, the pore-forming agent is used in from 50 parts by weight to 300 parts by weight per 100 parts by weight of the monomer mixture.

In the method for manufacturing porous resin particles in accordance with the present invention, the suspension polymerization may be carried out by, for example, dispersing droplets of a mixture containing the monomer mixture and the pore-forming agent in an aqueous phase containing an aqueous medium, an anionic surfactant, and a zwitterionic surfactant to polymerize the monomer mixture.

The monomer mixture is the one explained above and prepared by mixing the mono(meth)acrylate-based monomer in an amount of 3 wt % to 40 wt %, the other monofunctional vinyl-based monomer in an amount of 10 wt % to 69 wt %, and the polyfunctional vinyl-based monomer in an amount of 30 wt % to 70 wt %.

The non-polymerizable organic solvent as the pore-forming agent may be any publicly known organic solvent that renders porous the resin particles obtained by the manufacturing method above and that does not polymerize with the monomer mixture. Examples of the non-polymerizable organic solvent include aromatic compounds, such as toluene and benzene; acetate ester-based compounds, such as ethyl acetate and butyl acetate; and saturated aliphatic hydrocarbons, such as n-hexane, cyclohexane, n-octane, and n-dodecane. Any one of these non-polymerizable organic solvents may be used alone. Alternatively, two or more of them may be combined for use.

Of the non-polymerizable organic solvents above, acetate esters are excellent in rendering porous the resin particles obtained by the manufacturing method. Therefore, the pore-forming agent is preferably an acetate ester and more preferably ethyl acetate.

The pore-forming agent is used in an amount of preferably from 50 parts by weight to 300 parts by weight, and more preferably from 100 parts by weight to 300 parts by weight, per 100 parts by weight of the monomer mixture. If the pore-forming agent is used in an amount of less than 50 parts by weight, the resultant resin particles may not be sufficiently porous. Meanwhile, if the pore-forming agent is used in an amount of more than 300 parts by weight, the monomer mixture may not form droplets during suspension-polymerization of the monomer mixture.

The aqueous medium is by no means limited and may be, for example, water or a mixed medium of water and a water-soluble organic medium (methanol, ethanol, or another lower alcohol (alcohol with less than or equal to 5 carbon atoms)). The aqueous medium is typically used in an amount of from 100 parts by weight to 1000 parts by weight per 100 parts by weight of the monomer mixture to stabilize the resin particles.

The anionic surfactant may be any publicly known anionic surfactant that is used in the manufacture of resin particles. Examples of the anionic surfactant include fatty acid oils, such as sodium oleate and castor oil potassium; alkyl sulfate salts, such as sodium lauryl sulfate and ammonium lauryl sulfate; alkylbenzene sulfonate, such as sodium dodecyl benzene sulfonate; alkyl naphthalene sulfonic acid salts; alkane sulfonic acid salts; dialkyl sulfosuccinic acid salts, such as dioctyl sodium sulfosuccinate; phosphate ester salts, such as sodium polyoxyethylene alkyl phenyl ether phosphate and sodium polyoxyalkylene aryl ether phosphate; naphthalene sulfonate formalin condensate; polyoxyethylene alkyl phenyl ether sulfate salts; and polyoxyethylene alkyl sulfate salts. Any one of these anionic surfactants may be used alone. Alternatively, two or more of them may be combined for use.

The anionic surfactant is used in an amount of preferably from 0.005 to 0.1 parts by weight, and more preferably from 0.01 to 0.05 parts by weight, per 100 parts by weight of the aqueous medium. If the anionic surfactant is used in an amount of less than 0.005 parts by weight per 100 parts by weight of the aqueous medium, the monomer mixture may not readily form small droplets, which could hinder the manufacture of desired porous resin particles with high water and oil absorbance. Meanwhile, if the anionic surfactant is used in an amount of more than 0.1 parts by weight, fine resin particles may form in large quantities, which could hinder the manufacture of desired porous resin particles with high water and oil absorbance.

The zwitterionic surfactant may be any publicly known zwitterionic surfactant that is used in the manufacture of resin particles. Examples of the zwitterionic surfactant include lauryl dimethylamine oxide, betaine lauryl dimethylamino acetate, phosphate ester-based surfactants, and phosphite ester-based surfactants. Any one of these zwitterionic surfactants may be used alone. Alternatively, two or more of them may be combined for use.

The zwitterionic surfactant is used in an amount of preferably from 0.01 to 0.1 parts by weight, and more preferably from 0.02 to 0.05 parts by weight, per 100 parts by weight of the aqueous medium. If the zwitterionic surfactant is used in an amount of less than 0.01 parts by weight, particles may aggregate over the course of polymerization, which could hinder the manufacture of desired porous resin particles with high water and oil absorbance. Meanwhile, if the zwitterionic surfactant is used in an amount of more than 0.1 parts by weight, fine resin particles may form in large quantities, which could hinder the manufacture of desired porous resin particles with high water and oil absorbance.

A polymerization temperature for the monomer mixture is preferably in a range from 30° C. to 105° C. This polymerization temperature is preferably maintained for a period of 0.1 hours to 20 hours. When the polymerization is completed, a suspension (slurry) is obtained that contains porous resin particles that in turn contain a pore-forming agent in the particles. The suspension is distilled to remove the pore-forming agent. Preferably, after the dispersion stabilizer in the suspension is dissolved and removed, for example, with an acid, the porous resin particles are filtered out to remove the aqueous medium, washed in water or a solvent, and then dried, to isolate the porous resin particles.

In the suspension polymerization, typically, a polymerization initiator is added to the monomer mixture. Examples of the polymerization initiator include peroxides, such as benzoyl peroxide, lauroyl peroxide, tert-butyl peroxyisobutyrate; azo compounds, such as 2,2'-azobisisobutyronitrile, 2,2'-azobis(2,4-dimethylvaleronitrile), and 2,2-azobis-(2-methylpropionate) and peroxide salts, such as potassium persulfate and ammonium persulfate. Any one of these polymerization initiators may be used alone. Alternatively, two or more of them may be combined for use.

The polymerization initiator is used in an amount of preferably from 0.01 parts by weight to 10 parts by weight, and more preferably from 0.01 parts by weight to 5 parts by weight, per 100 parts by weight of the monomer mixture. If the polymerization initiator is used in an amount of less than 0.01 parts by weight per 100 parts by weight of the monomer mixture, the polymerization initiator does not readily react to initiate polymerization. Meanwhile, if the polymerization initiator is used in an amount of more than 10 parts by weight per 100 parts by weight of the monomer mixture, its cost performance is low.

In the suspension polymerization, the aqueous phase preferably contains a dispersion stabilizer to manufacture desired porous resin particles in a more stable manner. Examples of the dispersion stabilizer include inorganic oxides, such as silica and zirconium oxide; poorly water-soluble salts, such as barium carbonate, calcium carbonate, tribasic calcium phosphate, magnesium pyrophosphate, and calcium sulfate; and inorganic polymer substances, such as talc, bentonite, silicic acid, kieselguhr, and clay. Of these dispersion stabilizers, the dispersion stabilizer is preferably magnesium pyrophosphate prepared by double decomposition method to obtain porous resin particles with consistent particle diameters (especially, those with a coefficient of variation of particle diameters of less than or equal to 40%).

The dispersion stabilizer is used in an amount from preferably 0.1 parts by weight to 20 parts by weight, and more preferably from 0.5 parts by weight to 10 parts by weight, per 100 parts by weight of the monomer mixture. If the dispersion stabilizer is used in an amount of more than 20 parts by weight, the suspension may have too great viscosity to flow. Meanwhile, if the dispersion stabilizer is used in an amount of less than 0.1 parts by weight, the porous resin particles may disperse insufficiently and coalesce together.

To obtain porous resin particles with more consistent particle diameters, before the suspension polymerization, droplets are dispersed in a microfluidizer, a nanomizer, or another like high pressure disperser that exploits mutual collisions of droplets and collision force onto disperser walls for better dispersion.

Dispersion Liquid

The dispersion liquid in accordance with the present invention contains the porous resin particles described earlier and the hydrophilic dispersion medium described earlier. Since the porous resin particles in accordance with the present invention have excellent redispersibility, the dispersion liquid containing the porous resin particles in accordance with the present invention and the hydrophilic dispersion medium has excellent redispersibility.

The at least one hydrophilic dispersion medium selected from the group consisting of water and alcohol for use in the dispersion liquid in accordance with the present invention is by no means limited; examples include water, ethanol, 1-propanol, 2-propanol, glycerin, propylene glycol, and 1,3-butylene glycol. Any one of these hydrophilic dispersion media may be used alone. Alternatively, two or more of them may be mixed for use. The hydrophilic dispersion medium typically accounts for 20 wt % to 90 wt % of the dispersion liquid.

The dispersion liquid in accordance with the present invention may contain, apart from the porous resin particles and the hydrophilic dispersion media, oils, powders (pigments), fluorine compounds, surfactants, mucilaginous agents, preservatives, flavorings, ultraviolet protecting agents (both organic and inorganic, and may be adapted for either UV-A or UV-B), salts, solvents other than hydrophilic dispersion media, oxidation inhibitors, chelating agents, neutralizers, pH-adjusters, insect repellents, medical ingredients, pigments, and various other components.

The dispersion liquid in accordance with the present invention may contain small quantities of other resin components as long as they do not affect redispersibility and other desirable physical properties. Specific examples of the other resin components include vinyl chloride-based resins, such as vinyl chloride polymers and vinyl chloride-vinylidene chloride copolymers; vinyl ester-based resins, such as vinyl acetate polymers and vinyl acetate-ethylene copolymers; styrene-based resins, such as styrene polymers, styrene-acrylonitrile copolymers, styrene-butadiene-acrylonitrile copolymers, styrene-butadiene block copolymers, styrene-isoprene block copolymers, and styrene-methyl methacrylate copolymers; and (meth)acrylate ester-based resins, such as (meth)acrylic-based resins, (meth)acrylate ester-acrylonitrile copolymers, and (meth)acrylate ester-styrene copolymers.

Since the porous resin particles in accordance with the present invention have excellent redispersibility, a uniform dispersion liquid is readily obtainable by, for example, gentle mixing in a publicly known mixer, a disperser, or other like dispersing means.

External Preparation

The external preparation in accordance with the present invention contains the porous resin particles. Since the external preparation in accordance with the present invention has high water absorbance and high oil absorbance, it absorbs sweat and sebum and keeps the skin smooth and silky when applied to the skin. In addition, even if the porous resin particles have precipitated on the bottom of the container, the external preparation in accordance with the present becomes usable by shaking only lightly before use because the external preparation has excellent redispersibility in the hydrophilic dispersion medium. Furthermore, since the porous resin particles have good dispersibility in the hydrophilic dispersion medium, the external preparation in accordance with the present invention exhibits excellent applicability and spreading on the skin. The external preparation in accordance with the present invention is also advantageous for manufacturing in that the porous resin particles are readily dispersible in manufacturing.

The porous resin particle content of the external preparation in accordance with the present invention may be suitably specified according to the type of the external preparation, and is preferably from 1 wt % to 80 wt % and more preferably from 3 wt % to 70 wt %. If the porous resin particle content of the external preparation is less than 1 wt %, the porous resin particles may not produce appreciable effects. Meanwhile, if the porous resin particle content is more than 80 wt %, the extra content may not produce rewarding, noticeable effects, which is not cost-effective.

The external preparation in accordance with the present invention may be used, for example, as an external medicine or as a cosmetic material. The external medicine is by no means limited in any particular manner as long as it is applicable to the skin. Specific examples of the external medicine include cream, ointment, and emulsion. Specific examples of the cosmetic material include cleansing cosmetics, such as soap, body shampoo, facial cleansing cream, scrub cleanser, and toothpaste; makeup cosmetic materials, such as makeup powders, face powder (e.g., loose powder and pressed powder), makeup foundation (e.g., powder foundation, liquid foundation, and emulsion foundation), lipstick, lip balm, cheek color, eye makeup cosmetics, and nail polish; lotion preparations, such as pre-shave lotions and body lotions; external preparations for the body, such as body powder and baby powder; skin care products, such as skin lotion, cream, and milky lotion (cosmetic milky lotion); antiperspirants (liquid antiperspirants, solid antiperspirants, cream antiperspirants); skin packs; hair-washing cosmetics; hair coloring preparaions; hairdressing agents; fragrances; bath preparations; sunscreen agents; sun tanning agents; and shaving cream.

Of these external preparations, the makeup powders, face powder, powder foundation, body powder, baby powder, and other powder-based cosmetic materials (in other words, powdery cosmetic material) are suitable applications for the porous resin particles in accordance with the present invention because they show excellent water and oil absorbance if the porous resin particles are used in them.

The body shampoo, pre-shave lotion, body lotion, and other like dispersion liquid-based cosmetic materials are suitable external preparation applications for the porous resin particles in accordance with the present invention because they show excellent water and oil absorbance and excellent dispersibility if the porous resin particles are used in them.

The porous resin particles to be blended in the external preparation in accordance with the present invention may be treated with an oil; a surface treatment agent, such as a silicone compound or a fluorine compound; organic powder; or inorganic powder.

The oil may be any oil that is commonly used in external preparations. Examples of the oil include hydrocarbon oils, such as liquid paraffin, squalane, vaseline, and paraffin wax; higher fatty acids, such as lauric acid, myristic acid, palmitic acid, stearic acid, oleic acid, behenic acid, undecylenic acid, oxystearic acid, linoleic acid, lanolin fatty acid, and synthetic fatty acid; ester oils, such as glyceryl trioctanoate, propylene glycol dicaprate, cetyl 2-ethylhexanoate, isocetyl stearate; waxes, such as beeswax, spermaceti, lanolin, carnauba wax, and candelilla wax; fats and oils, such as linseed oil, cottonseed oil, castor oil, egg-yolk oil, and coconut oil; metal soaps, such as zinc stearate and zinc laurate; and higher alcohols, such as cetyl alcohol, stearyl alcohol, and oleyl alcohol. The porous resin particles may be treated with the oil by any method that is by no means limited in any particular manner. An example of such a method is a dry method in which oil is added to the porous resin particles, and the mixture is stirred in a mixer to coat the porous resin particles with the oil. Another example is a wet method in which oil is heated and dissolved in ethanol, propanol, ethyl acetate, hexane, or another appropriate solvent, the porous resin particles are added to the dissolved oil and mixed while stirring, and thereafter the solvent is removed under reduced pressure or by heating to coat the porous resin particles with the oil.

The silicone compound may be any compound that is commonly used in external preparations. Examples of the silicone compound include dimethylpolysiloxane, methylhydrogenpolysiloxane, methylphenylpolysiloxane, acrylsilicone graft polymer, organic silicone resin, and partially crosslinked organopolysiloxane polymer. The porous resin particles may be treated with the silicone compound by any method that is by no means limited in any particular manner. Examples of such a method include the dry and wet methods explained here. The silicone compound may be subjected to firing where necessary. For a reactive silicone compound, a reaction catalyst, as an example, may be added where appropriate.

The fluorine compound may be any compound that is commonly blended in external preparations. Examples of the fluorine compound include perfluoroalkyl group-containing esters, perfluoroalkyl silane, perfluoropolyether, and perfluoro group-containing polymers. The porous resin particles may be treated with the fluorine compound by any method that is also by no means limited in any particular manner. Examples of such a method include the dry and wet methods mentioned above. The fluorine compound may be subjected to firing where necessary. For a reactive fluorine compound, a reaction catalyst, as an example, may be added where appropriate.

Examples of the organic powder include natural macromolecular compounds, such as gum arabic, gum tragacanth, guar gum, locust bean gum, karaya gum, Irish moss, Quince seeds, gelatins, shellac, rosin, and casein; semisynthetic macromolecular compounds, such as sodium carboxymethyl cellulose, hydroxyethyl cellulose, methyl cellulose, ethyl cellulose, sodium alginate, gum ester, nitro cellulose, hydroxypropyl cellulose, and crystalline cellulose; polyvinyl alcohol; polyvinylpyrrolidone; sodium polyacrylate; carboxyvinyl polymers; polyvinyl methylether; polyamide resins; silicone oil; and resin particles, such as nylon particles, polymethyl methacrylate particles, crosslinked polystyrene particles, silicone-based particles, urethane particles, polyethylene particles, and fluororesin particles. Examples of the inorganic powder include iron oxides, ultramarines, ferric ferrocyanide, chromium oxides, chromium hydroxide, carbon black, manganese violet, titanium oxides, zinc oxides, talc, kaolin, mica, calcium carbonate, magnesium carbonate, isinglass, aluminum silicate, barium silicate, calcium silicate, magnesium silicate, silica, zeolite, barium sulfate, calcined calcium sulfate (calcined gypsum), calcium phosphate, hydroxyapatite, and ceramic powder. Any one of these organic and inorganic powders may be surface-treated in advance. Examples of the surface treatment include any publicly known surface treatment technology mentioned earlier.

A commonly used main agent or additives may be blended with the external preparation in accordance with the present invention where necessary as long as they do not negatively affect the effects of the invention. Examples of the main agent and additives include water, lower alcohols (alcohols with less than or equal to 5 carbon atoms), fats and oils, waxes, hydrocarbons, higher fatty acids, higher alcohols, sterols, fatty acid esters, metal soaps, moisturizing agents, surfactants, macromolecular compounds, color ingredients, fragrance, clay minerals, antiseptics, anti-inflammatory agents, antioxidants, ultraviolet absorbers, organic and inorganic composite particles, pH-adjusters (e.g., triethanolamine), specially mixed additives, and pharmaceutically active ingredient.

Specific examples of the fate and oils and waxes include avocado oil, almond oil, olive oil, cacao butter, beef tallow, sesame oil, wheat germ oil, safflower oil, shea butter, turtle oil, camellia oil, persic oil, castor oil, grape seed oil, macadamia nut oil, mink oil, egg-yolk oil, Japan wax, coconut oil, rose hip oil, hardened oil, silicone oil, orange roughy oil, carnauba wax, candelilla wax, spermaceti, jojoba oil, montan wax, beeswax, and lanolin.

Specific examples of the hydrocarbon include liquid paraffin, vaseline, paraffin, ceresin, microcrystalline wax, and squalane.

Specific examples of the higher fatty acid include fatty acids with 11 or more carbon atoms, such as lauric acid, myristic acid, palmitic acid, stearic acid, oleic acid, behenic acid, undecylenic acid, oxystearic acid, linoleic acid, lanolin fatty acid, and synthetic fatty acid.

Specific examples of the higher alcohol include alcohols with 6 or more carbon atoms, such as lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol, and decyltetradecanol.

Specific examples of the sterol include cholesterol, dihydrocholesterol, and phytocholesterol.

Specific examples of the fatty acid ester include linoleic acid esters, such as ethyl linoleate; lanolin fatty acid esters, such as isopropyl lanolate; lauric acid esters, such as hexyl laurate; myristic acid esters, such as isopropyl myristate, myristyl myristate, cetyl myristate, and octyldodecyl myristate; oleic acid esters, such as decyl oleate and octyldodecyl oleate; dimethyl octanoic acid esters, such as hexyldecyl dimethyloctanoate; isooctanoic acid esters, such as cetyl isooctanoate (cetyl 2-ethylhexanoate); palmitic acid esters, such as decyl palmitate; and cyclic alcohol fatty acid esters, such as glycerin trimyristate, glycerin tri(capryl caprate), propylene glycol dioleate, glycerin triisostearate, glycerin triisooctanoate, cetyl lactate, myristyl lactate, diisostearyl malate, cholesteryl isostearate, and cholesteryl 12-hydroxystearate.

Specific examples of the metal soap include zinc laurate, zinc myristate, magnesium myristate, zinc palmitate, zinc stearate, aluminum stearate, calcium stearate, magnesium stearate, and zinc undecylenate.

Specific examples of the moisturizing agent include glycerin, propylene glycol, 1,3-butylene glycol, polyethylene glycol, sodium dl-pyrrolidonecarboxylate, sodium lactate, sorbitol, sodium hyaluronate, polyglycerin, xylitol, and maltitol.

Specific examples of the surfactant include anionic surfactants, such as higher fatty acid soaps, higher alcohol sulfate esters, N-acyl glutamic acid salts, and phosphate ester salts; cationic surfactants, such as amine salts and quaternary ammonium salts; zwitterionic surfactants, such as betaine-type zwitterionic surfactants, amino acid-type zwitterionic surfactants, imidazoline-type zwitterionic surfactants, and lecithin; and non-ionic surfactants, such as fatty acid monoglyceride, polyethylene glycol, propylene glycol fatty acid ester, sorbitan fatty acid ester, sucrose fatty acid ester, polyglycerol fatty acid ester, and ethylene oxide condensates.

Specific examples of the macromolecular compound include natural macromolecular compounds, such as gum arabic, gum tragacanth, guar gum, locust bean gum, karaya gum, Irish moss, Quince seed, gelatin, shellac, rosin, and casein; semisynthetic macromolecular compounds, such as sodium carboxymethyl cellulose, hydroxyethyl cellulose, methyl cellulose, ethyl cellulose, sodium alginate, gum ester, nitro cellulose, hydroxypropyl cellulose, and crystal cellulose; synthetic macromolecular compounds, such as polyvinyl alcohols, polyvinylpyrrolidone, sodium polyacrylate, carboxyvinyl polymers, polyvinyl methylether, polyamide resin, silicone oil; and resin particles, such as nylon particles, poly(meth)acrylate particles (e.g., polymethyl methacrylate particles), polystyrene particles, silicone-based particles, urethane particles, polyethylene particles, and silica particles, Specific examples of the color ingredients include inorganic pigments, such as iron oxides (e.g., red iron oxide, yellow iron oxide, black iron oxide), ultramarines, iron blue, chromium oxide, chromium hydroxide, carbon black, manganese violet, titanium oxide, zinc oxide, talc, kaolin, calcium carbonate, magnesium carbonate, isinglass, aluminum silicate, barium silicate, calcium silicate, magnesium silicate, silica, zeolite, barium sulfate, calcined calcium sulfate (calcined gypsum), calcium phosphate, hydroxyapatite, and ceramic powder; and tar dyes, such as azo-based dyes, nitro-based dyes, nitroso-based dyes, xanthene-based dyes, quinoline-based dyes, anthraquinoline-based dyes, indigo-based dyes, triphenylmethane-based dyes, phthalocyanine-based dyes, and pyrene-based dyes.

The ingredient powder for macromolecular compounds and the ingredient powder for color materials may be surface-treated in advance before use. The surface treating method may be any publicly known surface treatment technology. Examples of the treatment include treatments with an oil, such as hydrocarbon oil, ester oil, or lanolin; treatments with a silicone, such as dimethylpolysiloxane, methylhydrogenpolysiloxane, or methylphenylpolysiloxane; treatments with a fluorine compound, such as perfluoroalkyl group-containing ester, peifluoroalkyl silane, perfluoropolyether, or perfluoroalkyl group-containing polymer; treatments with a silane coupling agent, such as 3-methacryloxypropyltrimethoxysilane or 3-glycidoxypropyltrimethoxysilane; treatments with a titanium coupling agent, such as isopropyltriisostearoyl titanate, or isopropyl tris(dioctylpyrophosphate) titanate; treatments with a metal soap; treatments with an amino acid, such as acyl glutamic acid; treatments with lecithin, such as hydrogenated egg-yolk lecithin; treatments with collagen; treatments with polyethylene; moisturizing treatments, treatments with an inorganic compound; and mechanochemical treatments.

Specific examples of the clay mineral include components that have several functions including those of extender pigments and adsorbents, such as talc, mica, sericite, titanium sericite (titanium oxide-coated sericite), white mica, and Veegum® manufactured by Vanderbilt.

Specific examples of the fragrance include anisaldehyde, benzyl acetate, and geraniol. Specific examples of the antiseptics include methylparapen, ethylparapen, propylparapen, benzalkonium, and benzethonium. Specific examples of the antioxidants include dibutylhydroxytoluene, butylhydroxyanisole, propyl gallate, and tocopherol. Specific examples of the ultraviolet absorber include inorganic absorbents, such as fine particles of titanium oxide, fine particles of zinc oxide, fine particles of cerium oxide, fine particles of iron oxide, and fine particles of zirconium oxide; and organic absorbents, such as benzoic acid-based absorbents, para-aminobenzoic acid-based absorbents, anthranilic acid-based absorbents, salicylic acid-based absorbents, cinnamic acid-based absorbents, benzophenone-based absorbents, and dibenzoyl methane-based absorbents.

Specific examples of the specially mixed additive include hormones, such as estradiol, estrone, ethinylestradiol, cortisone, hydrocortisone, and prednisone; vitamins, such as vitamin A, vitamin B, vitamin C, and vitamin E; skin astringents, such as citric acid, tartaric acid, lactic acid, aluminum chloride, aluminum potassium sulfate, allantoin chlorohydroxy aluminum, zinc para-phenolsulfonate, and zinc sulfate; trichogenous accelerants, such as cantharides tincture, capsicum tincture, ginger tincture, swertia extract, garlic extract, hinokitiol, carpronium chloride, glyceride pentadecanate, vitamin E, estrogen, and photosensitive elements; and whitening agents such as magnesium L-ascorbyl-phosphate and kojic acid.

Coating Material

The coating material in accordance with the present invention contains the porous resin particles. The coating material preferably contains a dispersion liquid mentioned earlier. In other words, the coating material preferably contains both the porous resin particles and the hydrophilic dispersion medium.

The coating material may contain a binder resin where necessary. The binder resin may be a resin soluble in the hydrophilic dispersion medium or an emulsion-type binder resin dispersible in the hydrophilic dispersion medium.

Examples of the binder resin include acrylic resins, alkyd resins, polyester resins, polyurethane resins, chlorinated polyolefin resins, and amorphous polyolefin resins. Any one of these binder resins may be selected as appropriate according to various conditions including the adhesion of the coating material to the base material to be coated and the environment in which the coating material is to be used.

The quantity of the porous resin particles in the coating material may vary depending on, for example, the thickness of the coating film to be formed, the average particle diameter of the porous resin particles, and coating methods. The quantity of the porous resin particles is preferably from 5 wt % to 50 wt %, more preferably from 10 wt % to 50 wt %, and even more preferably from 20 wt % to 40 wt %, as based on the sum of the binder resin (only the solid content if an emulsion-type resin is used) and the porous resin particles. If the quantity of the porous resin particles is less than 5 wt %, the porous resin particles may not produce sufficient matting effects. Meanwhile, if the quantity of the porous resin particles is more than 50 wt %, the coating material may have too great viscosity for the porous resin particles to sufficiently disperse, which could cause improper appearance, such as microcracks, in the resultant coating film or a rough surface of the coating film.

The coating material may contain, where necessary, a publicly known coating surface adjuster, a fluidity adjuster, an ultraviolet absorber, a light stabilizer, a curing catalyst, an extender pigment, a coloring pigment, a metal pigment, a mica powder pigment, a dye, or an organic solvent except for the hydrophilic dispersion medium.

A coating film may be formed of the coating material by any publicly known method. Examples of the method of forming a coating film using the coating material include spray coating, roll coating, and brush coating. The coating material may be diluted with a diluent to adjust its viscosity when necessary. Examples of the diluent include hydrocarbon-based solvents, such as toluene and xylene; ketones-based solvents, such as methyl ethyl ketones and methyl isobutyl ketones; ester-based solvents, such as ethyl acetate and butyl acetate; ether-based solvents, such as dioxane and ethylene glycol diethylether; water; and alcohol-based solvents. Any one of these diluents may be used alone. Alternatively, two or more of them may be mixed for use.

Light Diffusion Member

Of the coating materials containing the porous resin particles, those which contain a binder resin and which are transparent, i.e., those which contain a transparent binder resin and which do not contain a non-transparent material, such as a pigment or a dye, may be used as a light-diffusing coating material, such as a paper coating material or a light diffusion member coating material. When this is the case, the porous resin particles act as a light diffusing agent.

A light diffusion member in accordance with the present invention may be manufactured by coating a transparent base material as a base material with a light-diffusing coating material (light diffusion member coating material) to form a transparent coating film (light-diffusing coating).

Examples of the transparent base material include any material suitably selected from resin base materials made of a resin, such as polyethylene terephthalate (PET), polyesters, acrylic resins, polycarbonates, and polyamides and inorganic base materials, such as a transparent glass sheet. The thickness of the transparent base material is by no means limited in any particular manner, but preferably from 10 μm to 500 μm with ease in fabrication and handling taken into consideration. The light-diffusing coating may be formed by any publicly known method, such as reverse roll coating, gravure coating, die coating, comma coating, and spray coating. The thickness of the light-diffusing coating is by no means limited in any particular manner, but preferably from 1 μm to 100 μm and more preferably from 3 μm to 30 μm with, for example, light diffusibility and film strength taken into consideration.

Alternatively, a light diffusion member in accordance with the present invention may be manufactured by molding a light-diffusing resin composition prepared by dispersing the porous resin particles in accordance with the present invention as a light diffusing agent in a transparent base material resin (transparent resin).

Examples of the transparent base material resin include acrylic resins, alkyl(meth)acrylate styrene copolymers, polycarbonates, polyesters, polyethylenes, polypropylenes, and polystyrenes. Any one of these transparent base material resins may be used alone. Alternatively, two or more of them may be combined for use.

The porous resin particles are added to the transparent base material resin in an amount of preferably from 0.01 parts by weight to 40 parts by weight, and more preferably from 0.1 parts by weight to 10 parts by weight, per 100 parts by weight of the transparent base material resin. If the porous resin particles are added in an amount of less than 0.01 parts by weight, the resultant light diffusion member may not exhibit sufficient light diffusibility. If the porous resin particles are added in an amount of more than 40 parts by weight, the resultant light diffusion member exhibits sufficient light diffusibility, possibly, at the cost of the optical transparency of the light diffusion member.

The method for manufacturing the light-diffusing resin composition is by no means limited in any particular manner. The light-diffusing resin composition may be manufactured by mixing the porous resin particles and the transparent base material resin by a publicly known, conventional method, such as mechanical pulverization/crushing mixing. According to mechanical pulverization/crushing mixing, a light-diffusing resin composition may be manufactured by mixing and stirring the porous resin particles and the transparent base material resin using a Henschel mixer, a V-type mixer, a Turbula mixer, a hybridizer, a rocking mixer, or like apparatus.

The light diffusion member in accordance with the present invention is obtained by molding the light-diffusing resin composition. The light-diffusing resin composition in pellet form may be molded, for example, by injection molding, injection compression molding, or extrusion molding into a molded article (light diffusion member). Alternatively, the light-diffusing resin composition may be extrusion molded into a sheet-like molded article which is then further molded, for example, by vacuum molding or compressed air molding into a final molded article (light diffusion member).

EXAMPLES

The following will specifically describe the present invention by way of examples and comparative examples. The present invention is by no means limited to these examples. First, various measurement and evaluation methods used for the examples and comparative examples will be described: namely, a method of measuring the volume-average particle diameter and the coefficient of variation of resin particles, a method of measuring the specific surface area of resin particles, a method of measuring the pore diameter and pore volume of resin particles, a method of evaluating porosity, a method of measuring the water absorption value of resin particles, a method of measuring the oil absorption value of resin particles, a method of evaluating the hydrophilicity of resin particles, a method of evaluating the redispersibility of resin particles in ethanol, and a method of evaluating the redispersibility of resin particles in water, Method of Measuring Volume-Average Particle Diameter and Coefficient of Variation of Particle Diameters of Resin Particles The volume-average particle diameter of resin particles (arithmetic average diameter in a volume-based particle size distribution) was measured using a Coulter Multisizer II (measuring instrument manufactured by Beckman Coulter, Inc.). The measurement was carried out after calibration using an aperture of 50 μm as instructed in the reference MANUAL FOR THE COULTER MULTISIZER (1987) issued by Coulter Electronics Limited.

Specifically, 0.1 g of resin particles were preliminarily dispersed in 10 ml of a 0.1 wt % nonionic surfactant in a touch mixer ("TOUCHMIXER MT-31" manufactured by Yamato Scientific Co., Ltd.) and an ultrasonic cleaner ("ULTRASONIC CLEANER VS-150" manufactured by Velvo-Clear) to obtain a dispersion liquid. Next, a beaker was filled with ISOTON® II (measurement electrolyte solution available from Beckman Coulter, Inc.) which came with the Coulter Multisizer II, and the dispersion liquid was added dropwise into the beaker using a dropper while gently stirring in order to calibrate the concentration meter on the screen of the Coulter Multisizer II to read about 10%. Next, an aperture size (diameter) of 50 μm, an aperture current of 800 μA, a gain of 4, and positive polarity (for the inner electrode) were entered on the Coulter Multisizer II, and the measurement was carried out in manual mode. Over the course of the measurement, the content of the beaker was stirred so gently that no bubbles could enter the beaker. The measurement was ended when the measurement was done on 100,000 particles. The measured particle diameters of 100,000 particles were averaged to obtain a volume-average particle diameter (arithmetic average diameter in a volume-based particle size distribution).

The coefficient of variation (CV) for the particle diameters of resin particles was calculated using the following equation.

Coefficient of Variation of Particle Diameters of Resin Particles=(Standard Deviation of Volume-based Particle Size Distribution of Resin Particles/Volume-average Particle Diameter of Resin Particles)×100

Method of Measuring Specific Surface Area of Resin Particles

The specific surface area of resin particles was measured by the BET method (nitrogen adsorption method described in JIS R1626). BET nitrogen adsorption isotherm were measured for target resin particles using an automatic specific surface area and porosimetry analyzer Tristar 3000 manufactured by Shimadzu Corporation, and a specific surface area was calculated from nitrogen adsorption levels by the BET multi-point method. Note that the nitrogen adsorption isotherm were measured by a constant volume method using nitrogen as the adsorbate with the adsorbate cross-sectional area being 0.162 nm².

Table 2 shows the measured specific surface area of the resin particles of examples 1 to 9 and comparative examples 1, 2, and 5.

Method of Measuring Pore Diameter and Pore Volume of Resin Particles

The pore diameter (average pore diameter) and pore volume of the resin particles were determined by the BJH method. Nitrogen adsorption isotherm were measured for target resin particles using an automatic specific surface area and porosimetry analyzer Tristar 3000 manufactured by Shimadzu Corporation, and a pore diameter (average pore diameter) and a pore volume (integral pore volume) were calculated by the BJH method. Note that the nitrogen adsorption isotherm were measured by a constant volume method using nitrogen as the adsorbate with the adsorbate cross-sectional area being 0.162 nm².

Table 2 shows the measured pore diameter and pore volume of the resin particles of examples 1 to 9 and comparative examples 1 and 2.

Evaluating Porosity of Resin Particles

Resin particles were rated porous (indicated by "P") if their specific surface area as obtained by the measuring method above was from 3 m²/g to 300 m²/g AND if their pore diameter was from 4 nm to 20 nm. They were rated non-porous (indicated by "NP") if their specific surface area was not from 3 m²/g to 300 m²/g and/or if their pore diameter is not from 4 nm to 20 nm.

Table 2 shows evaluations of porosity of the resin particles of examples 1 to 9 and comparative examples 1, 2 and 5.

Method of Measuring Water Absorption Value of Resin Particles

The water absorption value of resin particles were measured by a modified JIS K 5101-13-2 measuring method. Distilled water was used instead of boiled linseed oil, and a new criterion was used to determine an end point. Details of the measurement of water absorption values follow.

(A) Devices and Tools

Measurement plate: Flat and smooth glass plate larger than 300 mm×400 mm×5 mm

Palette knife (spatula): Steel or stainless steel blade with handle

Chemical balance (weighing scales): Capable of measuring down to order of 10 mg

Burette: 10 ml capacity as specified in JIS R 3505

(B) Reagent: Distilled water (C) Measuring Method (1) One gram of resin particles was placed at the center of a measurement plate. Four or five droplets of distilled water were slowly added at a time from the burette to the center of the resin particles. Every time droplets were added, both the resin particles and the distilled water were thoroughly kneaded with a palette knife.

(2) The dropwise addition and kneading were repeated until the whole resin particles and distilled water formed a hard putty-like mass. After that, one droplet of distilled water was added at a time and kneaded. An end point was regarded as having been reached when the addition of a droplet of distilled water abruptly softened the paste (kneaded article of resin particles plus distilled water) so that the paste started to flow.

(3) Determining Flow

The paste was determined to have flown if the addition of a droplet of distilled water abruptly softened the paste so that the paste moved when the measurement plate was erected upright. If the paste does not move on the vertically erected measurement plate, another droplet of distilled water was added.

(4) The amount of distilled water consumed up to the end point, as indicated by the decrease in the amount of the liquid in the burette, was read off the burette.

(5) Each measurement was completed within 7 to 15 minutes. If the measurement lasted longer than 15 minutes, the measurement was started all over again. Only those results from measurements that were completed within the specified period were accepted.

(D) Calculating Water Absorption value

The water absorption value per 100 g of the sample was calculated using the following equation:

$$W=(V/m)\times 100$$

where W is a water absorption value (ml/100 g), m is the mass of resin particles (g), and V is the volume of consumed distilled water (ml).

Table 2 shows the measured water absorption values of the resin particles of examples 1 to 9 and comparative example 2 and 5.

Method of Measuring Oil Absorption Value of Resin Particles

The oil absorption value of resin particles were measured by a modified JIS K 5101-13-2 measuring method. Purified linseed oil was used instead of boiled linseed oil, and a new criterion was used to determine an end point. Details of the measurement of oil absorption values follow.

(A) Devices and Tools

Measurement plate: Flat and smooth glass plate larger than 300 mm×400 mm×5 mm

Palette knife (spatula): Steel or stainless steel blade with handle

Chemical balance (weighing scales): Capable of measuring down to order of 10 mg

Burette: 10 ml capacity as specified in JIS R 3505

(B) Reagent

Purified linseed oil: As specified in ISO 150 (JIS first grade manufactured by Wako Pure Chemical Industries Ltd.)

(C) Measuring Method (1) One gram of resin particles was placed at the center of a measurement plate. Four or five droplets of purified linseed oil were slowly added at a time from the burette to the center of the resin particles. Every time droplets were added, both the resin particles and the purified linseed oil were thoroughly kneaded with a palette knife.

(2) The dropwise addition and kneading were repeated until the whole resin particles and purified linseed oil formed a hard putty-like mass. After that, one droplet of purified linseed oil was added at a time and kneaded. An end point was regarded as having been reached when the addition of a droplet of purified linseed oil abruptly softened the paste (kneaded article of resin particles and purified linseed oil) so that the paste started to flow.

(3) Determining Flow

The paste was determined to have flown if the addition of a droplet of purified linseed oil abruptly softened the paste so that the paste moved when the measurement plate was erected upright. If the paste does not move on the vertically erected measurement plate, another droplet of purified linseed oil was added.

(4) The amount of purified linseed oil consumed up to the end point, as indicated by the decrease in the amount of the liquid in the burette, was read off the burette.

(5) Each measurement was completed within 7 to 15 minutes. If the measurement lasted longer than 15 minutes, the measurement was started all over again. Only those results from measurements that were completed within the specified period were accepted.

(D) Calculating Oil Absorption value

The oil absorption value per 100 g of the sample was calculated using the following equation:

$$O=(V/m)\times 100$$

where O is an oil absorption value (ml/100 g), m is the mass of resin particles (g), and V is the volume of consumed purified linseed oil (ml).

Table 2 shows the measured oil absorption values of the resin particles of examples 1 to 9 and comparative examples 1, 2, and 5.

Evaluating Hydrophilicity of Resin Particles

After putting 100 ml of distilled water in a glass beaker (capacity: 100 ml), 0.2 g of resin particles were floated on the water surface, and the top of the glass beaker was sealed with plastic wrap. Thereafter, the glass beaker was let to stand to observe precipitation of the resin particles. The time that the resin particles took to precipitate was measured. In this evaluation of hydrophilicity, the resin particles were rated very hydrophilic (indicated by "VH") if they precipitated completely in less than 2 hours after they were let to stand, sufficiently hydrophilic (indicated by "S") if they precipitated completely in 2 hours to less than 12 hours after they were let to stand, poorly hydrophilic (indicated by "PH") if they precipitated completely in 12 hours to less than 24 hours after they were let to stand, and very poorly hydrophilic (indicated by "VPH") if no particles precipitated at all in 24 hours after they were let to stand.

Table 2 shows evaluations of hydrophilicity of the resin particles of examples 1 to 9 and comparative examples 1, 2 and 5.

Evaluating Redispersibility of Resin Particles in Ethanol

Resin particles (0.5 g) were weighed out in a graduated test tube manufactured by Maruemu Corporation (product name: "Screw Capped Test Tube NR-10"). After 10 ml of commercially available absolute ethanol (99.5 vol % or more pure) was added to the weighed-out resin particles, the resin particles were dispersed in the ethanol using a touch mixer (mag-mixer of touch drive-type) until the resin particles are completely dispersed in the ethanol. The dispersion liquid hence became entirely clouded (the dispersion liquid had a volume of about 10 ml).

Next, the test tube was let to stand for 12 hours to precipitate the resin particles. Then, the test tube was shaken by hand to redisperse the resin particles in the ethanol. The number of times the test tube needed to be shaken to redisperse the resin particles in the ethanol was recorded to evaluate how easily the resin particles redispersed.

In the evaluation of the redispersibility of the resin particles of the examples and comparative examples of the invention in ethanol, the test tube was shaken by hand to produce a uniform mixture. The number of shakes needed to uniformly disperse all the precipitated resin particles in ethanol was used as an indicator in the evaluation of the redispersibility of resin particles. Swinging the test tube reciprocally once with an amplitude of about 10 cm was counted as one complete shake. The dispersion of the resin particles was visually checked for each shake to determine the number of shakes needed to uniformly disperse all the precipitated resin particles.

In the evaluation of redispersibility in ethanol, the resin particles were rated acceptable (indicated by "A") if they took 60 or fewer shakes to be thoroughly and uniformly dispersed and non-acceptable (indicated by "NA") if they took more than 60 shakes to be thoroughly and uniformly dispersed.

Table 2 shows evaluations of the redispersibility of the resin particles of examples 1 to 9 and comparative examples 1, 2 and 5 in ethanol.

Evaluating Redispersibility of Resin Particles in Water

Resin particles (0.5 g) were weighed out in a graduated test tube manufactured by Maruemu Corporation (product name: "Screw Capped Test Tube NR-10"). After 10 ml of distilled water was added to the weighed-out resin particles, the resin particles were dispersed in the water by repeatedly mixing in a touch mixer (mag-mixer of touch drive-type) and applying ultrasonic waves using an ultrasonic cleaner manufactured by Velvo-Clear ("ULTRASONIC CLEANER VS-150") until the resin particles are completely dispersed in the water. The dispersion liquid hence became entirely clouded (the dispersion liquid has a volume of about 10 ml).

Next, the test tube was let to stand for 12 hours to precipitate the resin particles. Then, the test tube was shaken by hand to redisperse the resin particles in the water. The number of times the test tube needed to be shaken to redisperse the resin particles in the water was recorded to evaluate how easily the resin particles redispersed.

In the evaluation of the redispersibility of the resin particles of the examples and comparative examples of the invention in water, the test tube was shaken by hand to produce a uniform mixture. The number of shakes needed to uniformly disperse all the precipitated resin particles in water was used as an indicator in the evaluation of the redispersibility of the resin particles. Swinging the test tube reciprocally once with an amplitude of about 10 cm was counted as one complete shake. The dispersion of the resin particles was visually checked for each shake to determine the number of shakes needed to uniformly disperse all the precipitated resin particles.

In the evaluation of redispersibility in water, the resin particles were rated acceptable (indicated by "A") if they took 80 or fewer shakes to be thoroughly and uniformly dispersed and non-acceptable (indicated by "N.A.") if they took more than 80 shakes to be thoroughly and uniformly dispersed.

Table 2 shows evaluations of the redispersibility of the resin particles of examples 1 to 9 and comparative examples 2 and 5 in water.

Example 1

A 5-L autoclave equipped with a stirrer and a thermometer was charged with an aqueous solution in which sodium lauryl sulfate (0.24 g, or 0.01 parts by weight per 100 parts by weight of water) as an anionic surfactant and 35% betaine lauryl dimethylamino acetate (1.37 g, or an equivalent of 0.02 parts by weight of pure betaine lauryl dimethylamino acetate per 100 parts by weight of water) as a zwitterionic surfactant were dissolved in 2400 g of water (aqueous medium). Then, magnesium pyrophosphate (48 g) prepared by double decomposition method as a dispersion stabilizer was dispersed in the aqueous solution in the autoclave to obtain a dispersion liquid (aqueous phase).

Methyl methacrylate (MMA) (330 g, or 55 wt % as based on the total monomers) as another monofunctional vinyl-based monomer, 30 g (5 wt % as based on the total monomers) of a poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) as a mono(meth)acrylate-based monomer, 240 g (40 wt % as based on the total monomers) of ethylene glycol dimethacrylate (EGDMA) as a polyfunctional vinyl-based monomer, 600 g (100 parts by weight per 100 parts by weight of the total monomers) of ethyl acetate as a pore-forming agent, and 1.8 g of 2,2'-azobis(2,4-dimethylvaleronitrile) as a polymerization initiator were mixed and dissolved to prepare a monomer mixture solution.

The monomer mixture solution prepared in advance was poured into the dispersion liquid (aqueous phase) in the autoclave. The content of the autoclave was stirred with a high-speed emulsifier/disperser (trade name: "T.K. Homomixer," manufactured by Primix Corporation) at a rotational speed of 6000 rpm for 10 minutes, to prepare a suspension of the monomer mixture solution with a droplet diameter of approximately 8 μm. Next, the internal temperature of the autoclave was raised to 50° C. to start the suspension polymerization of the monomer mixture solution while stirring the content of the autoclave. The monomer mixture solution was continuously heated at 70° C. for 2 hours to undergo suspension polymerization, to obtain a slurry.

Thereafter, while maintaining the jacket of the autoclave at 70° C., the internal pressure was reduced to −500 mmHg to remove ethyl acetate from the slurry. The slurry in the autoclave was then cooled down. Hydrochloric acid was added until the slurry showed a pH of 2 or less to decompose magnesium pyrophosphate. The slurry was washed in water and dehydrated in a centrifugal dehydrator to obtain a cake. The cake was dried in a vacuum in a vacuum drier at 80° C. and put through a sieve with 45 μm openings, to obtain the target resin particles.

The obtained resin particles had an average particle diameter of 7.9 μm and a coefficient of variation of particle diameters of 35.3%.

The resin particles were imaged under a scanning electron microscope (SEM). They turned out to be spherical and porous with multiple pores.

Example 2

The same procedures were followed as in example 1 except that: methyl methacrylate (MMA) was used in 300 g (50 wt % as based on the total monomers); and poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 60 g (10 wt % as based on the total monomers), to obtain resin particles.

The obtained resin particles had a volume-average particle diameter of 7.8 μm and a coefficient of variation of particle diameters of 35.2%.

The resin particles were imaged under a scanning electron microscope (SEM). They turned out to be spherical and porous with multiple pores.

Example 3

The same procedures were followed as in example 1 except that: methyl methacrylate (MMA) was used in 270 g (45 wt % as based on the total monomers); and poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 90 g (15 wt % as based on the total monomers), to obtain resin particles.

The obtained resin particles had a volume-average particle diameter of 8.5 μm and a coefficient of variation of particle diameters of 36.5%.

The resin particles were imaged under a scanning electron microscope (SEM). They turned out to be spherical and porous with multiple pores as shown in the SEM image in FIG. 1.

Example 4

The same procedures were followed as in example 1 except that: methyl methacrylate (MMA) was used in 120 g (30 wt % as based on the total monomers); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 80 g (20 wt % as based on the total monomers); ethylene glycol dimethacrylate (EGDMA) as a polyfunctional vinyl-based monomer was used in 200 g (50 wt % as based on the total monomers); ethyl acetate as a pore-forming agent was used in 800 g (200 parts by weight per 100 parts by weight of the total monomers); and 2,2'-azobis(2,4-dimethylvaleronitrile) as a polymerization initiator was used in 1.6 g, to obtain resin particles.

The obtained resin particles had a volume-average particle diameter of 8.0 μm and a coefficient of variation of particle diameters of 35.3%.

The resin particles were imaged under a scanning electron microscope (SEM). They turned out to be spherical and porous with multiple pores.

Example 5

The same procedures were followed as in example 1 except that: methyl methacrylate (MMA) was used in 120 g (25 wt % as based on the total monomers); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 120 g (25 wt % as based on the total monomers); ethylene glycol dimethacrylate (EGDMA) as a polyfunctional vinyl-based monomer was used in 240 g (50 wt % as based on the total monomers); ethyl acetate as a pore-forming agent was used in 720 g (150 parts by weight per 100 parts by weight of the total monomers); and 2,2'-azobis(2,4-dimethylvaleronitrile) as a polymerization initiator was used in 2.0 g, to obtain resin particles.

The obtained resin particles had a volume-average particle diameter of 9.5 μm and a coefficient of variation of particle diameters of 38.1%.

The resin particles were imaged under a scanning electron microscope (SEM). They turned out to be spherical and porous with multiple pores.

Example 6

The same procedures were followed as in example 1 except that: methyl methacrylate (MMA) was used in 96 g (20 wt % as based on the total monomers); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 144 g (30 wt % as based on the total monomers); ethylene glycol dimethacrylate (EGDMA) as a polyfunctional vinyl-based monomer was used in 240 g (50 wt % as based on the total monomers); ethyl acetate as a pore-forming agent was used in 720 g (150 parts by weight per 100 parts by weight of the total monomers); and 2,2'-azobis(2,4-dimethylvaleronitrile) as a polymerization initiator was used in 2.0 g, to obtain resin particles.

The obtained resin particles had a volume-average particle diameter of 10.4 μm and a coefficient of variation of particle diameters of 39.8%.

The resin particles were imaged under a scanning electron microscope (SEM). They turned out to be spherical and porous with multiple pores.

Example 7

The same procedures were followed as in example 1 except that: 96 g (20 wt % as based on the total monomers) of lactone-modified hydroxyethyl methacrylate (trade name: "Placcel® FM3," manufactured by Daicel Corporation, a compound of general formula (2), where R is $CH_3$, and p is 3) was used instead of poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average); methyl methacrylate (MMA) was used in 144 g (30 wt % as based on the total monomers); ethylene glycol dimethacrylate (EGDMA) as a polyfunctional vinyl-based monomer was used in 240 g (50 wt % as based on the total monomers); ethyl acetate as a pore-forming agent was used in 720 g (150 parts by weight per 100 parts by weight of the total monomers); and 2,2'-azobis(2,4-dimethylvaleronitrile) as a polymerization initiator was used in 2.0 g, to obtain resin particles.

The obtained resin particles had a volume-average particle diameter of 9.5 μm and a coefficient of variation of particle diameters of 38.1%.

The resin particles were imaged under a scanning electron microscope (SEM). They turned out to be spherical and porous with multiple pores as shown in the SEM image in FIG. 2.

Example 8

The same procedures were followed as in example 1 except that: 168 g (35 wt % as based on the total monomers) of methacrylic acid ethyl (EMA) was used instead of methyl methacrylate (MMA); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 72 g (15 wt % as based on the total monomers); ethylene glycol dimethacrylate (EGDMA) as a polyfunctional vinyl-based monomer was used in 240 g (50 wt % as based on the total monomers); ethyl acetate as a pore-forming agent was used in 720 g (150 parts by weight per 100 parts by weight of the total monomers); and 2,2'-azobis(2,4-dimethylvaleronitrile) as a polymerization initiator was used in 2.0 g, to obtain resin particles.

The obtained resin particles had a volume-average particle diameter of 7.9 μm and a coefficient of variation of particle diameters of 36.8%.

The resin particles were imaged under a scanning electron microscope (SEM). They turned out to be spherical and porous with multiple pores as shown in the SEM image in FIG. 3.

Example 9

The same procedures were followed as in example 1 except that: methyl methacrylate (MMA) was used in 72 g (15 wt % as based on the total monomers); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 72 g (15 wt % as based on the total monomers); ethylene glycol dimethacrylate (EGDMA) as a polyfunctional vinyl-based monomer was used in 336 g (70 wt % as based on the total monomers); ethyl acetate as a pore-forming agent was used in 720 g (150 parts by weight per 100 parts by weight of the total monomers); and 2,2'-azobis(2,4-dimethylvaleronitrile) as a polymerization initiator was used in 2.0 g, to obtain resin particles.

The obtained resin particles had a volume-average particle diameter of 8.2 μm and a coefficient of variation of particle diameters of 34.8%.

The resin particles were imaged under a scanning electron microscope (SEM). They turned out to be spherical and porous with multiple pores.

Comparative Example 1

The same procedures were followed as in example 1 except that: no poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used; and methyl methacrylate (MMA) was used in 360 g (60 wt % as based on the total monomers), to obtain resin particles.

The obtained resin particles had a volume-average particle diameter of 8.3 μm and a coefficient of variation of particle diameters of 35.8%.

Figure 4:
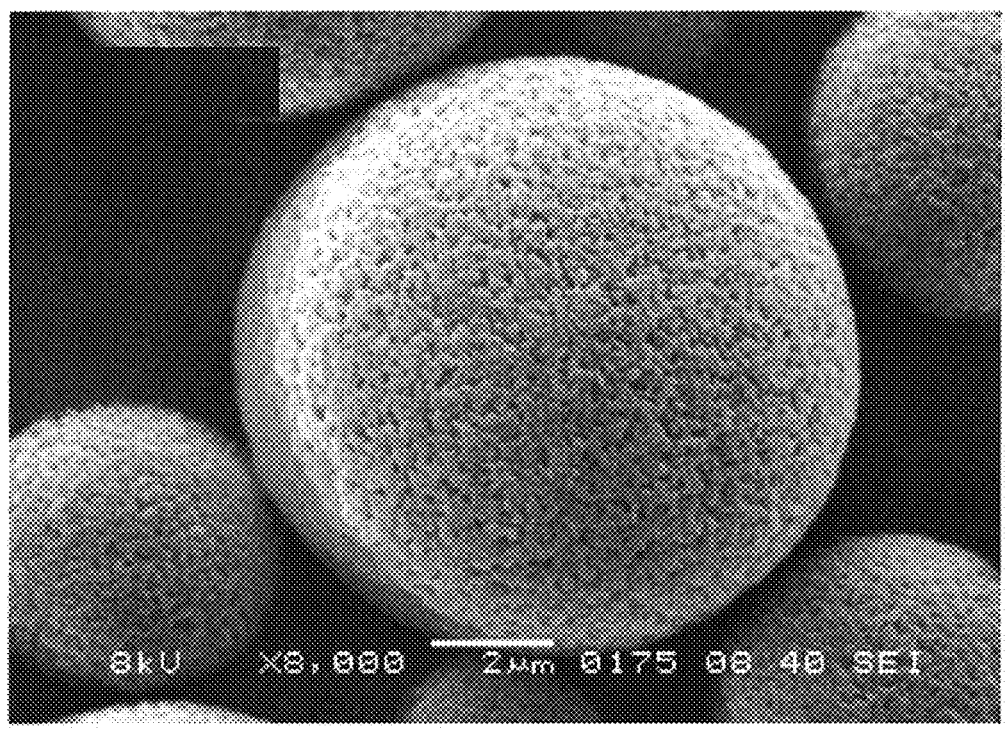
FIG. 4 is a scanning electron microscope (SEM) image of porous resin particles in accordance with comparative example 1.

The resin particles were imaged under a scanning electron microscope (SEM). They turned out to be spherical and porous with multiple pores as shown in the SEM image in FIG. 4.

Comparative Example 2

The same procedures were followed as in example 1 except that: methyl methacrylate (MMA) was used in 354 g (59 wt % as based on the total monomers); and poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 6 g (1 wt % as based on the total monomers), to obtain resin particles.

The obtained resin particles had a volume-average particle diameter of 7.9 μm and a coefficient of variation of particle diameters of 36.4%.

Figure 5:
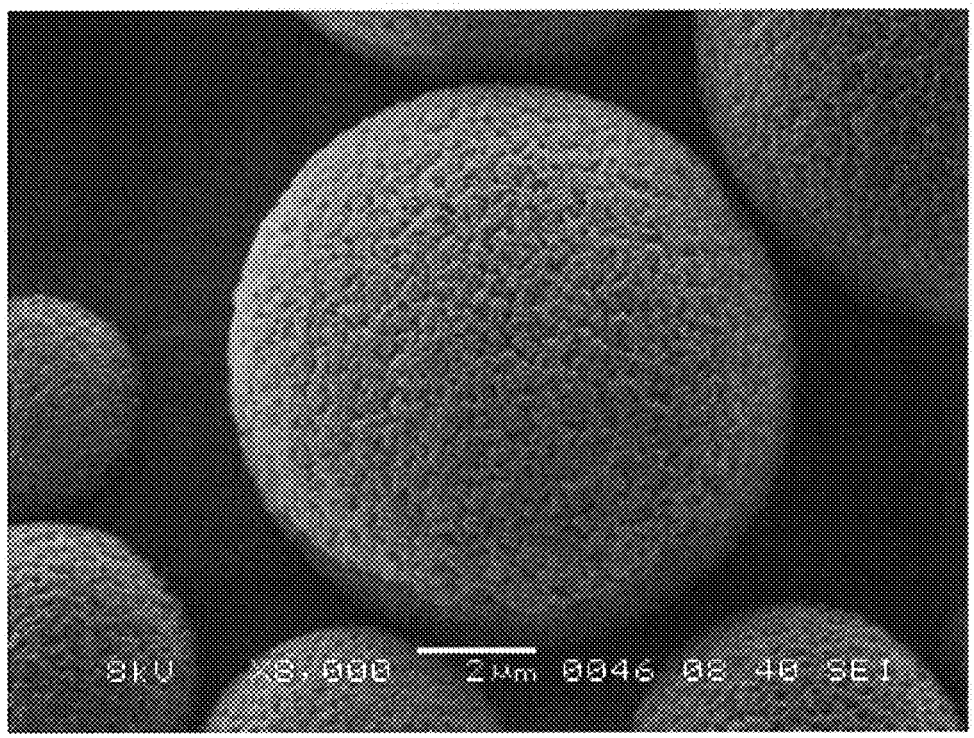
FIG. 5 is a scanning electron microscope (SEM) image of porous resin particles in accordance with comparative example 2.

The resin particles were imaged under a scanning electron microscope (SEM). They turned out to be spherical and porous with multiple pores as shown in the SEM image in FIG. 5.

Comparative Example 3

The same procedures were followed as in example 1 except that: no 35% betaine lauryl dimethylamino acetate was used; sodium lauryl sulfate was used in 0.72 g (0.03 parts by weight per 100 parts by weight of water); methyl methacrylate (MMA) was used in 270 g (45 wt % as based on the total monomers); and poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 90 g (15 wt % as based on the total monomers), in a failed attempt to obtain resin particles. The resin particles aggregated during the course of polymerization, and no fine resin particles were obtainable.

Comparative Example 4

The same procedures were followed as in example 1 except that: no sodium lauryl sulfate was used; 35% betaine lauryl dimethylamino acetate was used in 2.06 g (equivalent of 0.03 parts by weight of pure betaine lauryl dimethylamino acetate per 100 parts by weight of water); methyl methacrylate (MMA) was used in 270 g (45 wt % as based on the total monomers); and poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 90 g (15 wt % as based on the total monomers), in a failed attempt to obtain resin particles. The resin particles aggregated during the course of polymerization, and no fine resin particles were obtainable.

Comparative Example 5

The same procedures were followed as in example 1 except that: none of sodium lauryl sulfate, 35% betaine lauryl dimethylamino acetate, and ethyl acetate was used; methyl methacrylate (MMA) was used in 960 g (80 wt % as based on the total monomers); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 180 g (15 wt % as based on the total monomers); and ethylene glycol dimethacrylate (EGDMA) was used in 60 g (5 wt % as based on the total monomers), to obtain resin particles.

The obtained resin particles had a volume-average particle diameter of 7.2 μm and a coefficient of variation of particle diameters of 34.2%.

Figure 6:
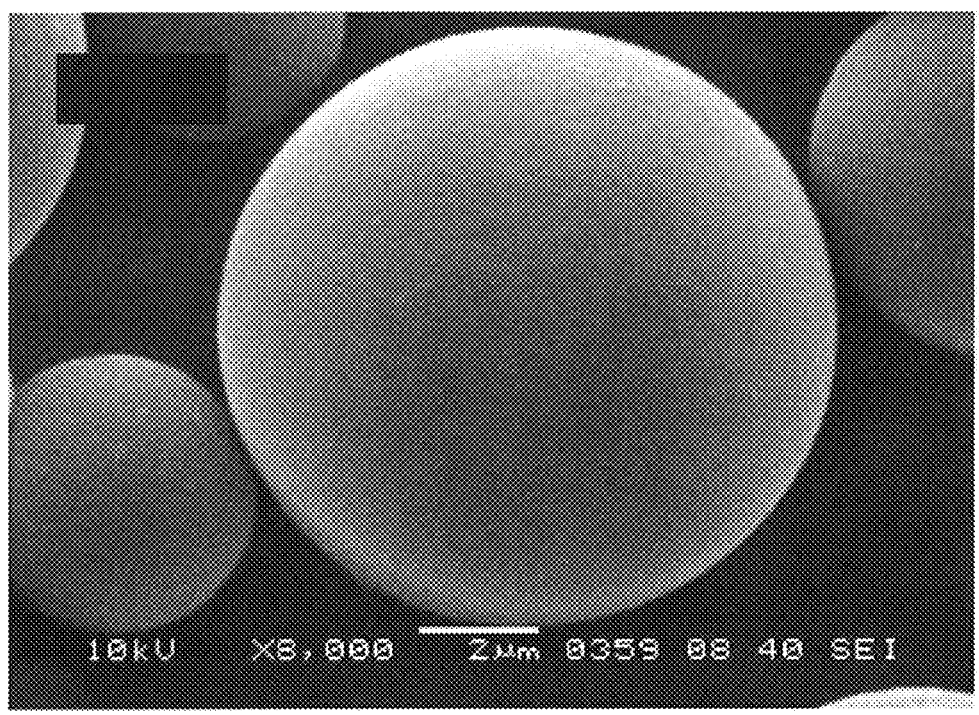
FIG. 6 is a scanning electron microscope (SEM) image of porous resin particles in accordance with comparative example 5.

The resin particles were imaged under a scanning electron microscope (SEM), which showed that the obtained resin particles were spherical, but not porous as shown in the SEM image in FIG. 6.

Comparative Example 6

The same procedures were followed as in example 1 except that: methyl methacrylate (MMA) was used in 48 g (10 wt % as based on the total monomers); poly(ethylene glycol-propylene glycol) monomethacrylate (trade name: "Blemmer® 50 PEP-300," manufactured by NOF Corporation, a mixture of compounds of general formula (1), where R is $CH_3$, l is about 3.5 on average, and m is about 2.5 on average) was used in 240 g (50 wt % as based on the total monomers); and ethylene glycol dimethacrylate (EGDMA) as a polyfunctional vinyl-based monomer was used in 192 g (40 wt % as based on the total monomers), in a failed attempt to obtain resin particles. The resin particles aggregated during the course of polymerization, and no fine resin particles were obtainable.

Table 1 shows the composition of monomer mixture, the amount of pore-forming agent used per 100 parts by weight of monomer mixture, the amount of anionic surfactant used per 100 parts by weight of water, and the amount of zwitterionic surfactant used per 100 parts by weight of water for the resin particles of examples 1 to 9 and comparative examples 1 to 6. Table 2 shows the measurement of specific surface area, the measurement of pore diameter, the measurement of pore volume, the evaluation of porosity, the measurement of water absorption value, the measurement of oil absorption value, the evaluation of hydrophilicity, the evaluation of redispersibility in ethanol, and the evaluation of redispersibility in water for the resin particles of examples 1 to 9 and comparative examples 1, 2, and 5. In comparative example 3, 4, and 6, since the resin particles aggregated during the course of polymerization, and no fine resin particles were obtainable, the specific surface area and the pore diameter were not measured, and the porosity, the hydrophilicity, the redispersibility in ethanol, and the redispersibility in water were not evaluated. The resin particles of comparative example 1 did not disperse in distilled water in the evaluation of hydrophilicity. The water absorption value of the resin particles of comparative example 1 could not be measured because distilled water did not infiltrate into them. The redispersibility of the resin particles of comparative example 1 in water could not be evaluated because the resin particles did not disperse in distilled water. The pore diameter and pore volume of the resin particles of comparative example 5 were not measured because they had very small specific surface area and were not porous.

TABLE 1

| | | Other Monofunctional Vinyl-based Monomer | | Mono(meth)acrylate-based Monomer | | Polyfunctional Vinyl-based Monomer | Pore-forming Agent EthylAcetate | Anionic Surfactant Sodium Lauryl Sulfate | Zwitterionic Surfactant Betaine Lauryl Dimethylamino Acetate |
|---|---|---|---|---|---|---|---|---|---|
| | | | | Blemmer® | Placcel® | | | | |
| | | MMA Relative Amt. to Total Monomers (wt %) | ENA Relative Amt. to Total Monomers (wt %) | 50 PEP-300 Relative Amt. to Total Monomers (wt %) | FM3 Relative Amt. to Total Monomers (wt %) | EGDMA Relative Amt. to Total Monomers (wt %) | Amt. Used Per 100 pbw of Total Monomers (pbw) | Amt. Used Per 100 pbw of Water (pbw) | Amt. Used Per 100 pbw of Water (pbw) |
| Ex. | 1 | 55 | 0 | 5 | 0 | 40 | 100 | 0.01 | 0.02 |
| | 2 | 50 | 0 | 10 | 0 | 40 | 100 | 0.01 | 0.02 |
| | 3 | 45 | 0 | 15 | 0 | 40 | 100 | 0.01 | 0.02 |
| | 4 | 30 | 0 | 20 | 0 | 50 | 200 | 0.01 | 0.02 |
| | 5 | 25 | 0 | 25 | 0 | 50 | 150 | 0.01 | 0.02 |
| | 6 | 20 | 0 | 30 | 0 | 50 | 150 | 0.01 | 0.02 |
| | 7 | 30 | 0 | 0 | 20 | 50 | 150 | 0.01 | 0.02 |
| | 8 | 0 | 35 | 15 | 0 | 50 | 150 | 0.01 | 0.02 |
| | 9 | 15 | 0 | 15 | 0 | 70 | 150 | 0.01 | 0.02 |
| Comp. Ex. | 1 | 60 | 0 | 0 | 0 | 40 | 100 | 0.01 | 0.02 |
| | 2 | 59 | 0 | 1 | 0 | 40 | 100 | 0.01 | 0.02 |
| | 3 | 45 | 0 | 15 | 0 | 40 | 100 | 0.03 | 0 |
| | 4 | 45 | 0 | 15 | 0 | 40 | 100 | 0 | 0.03 |
| | 5 | 80 | 0 | 15 | 0 | 5 | 0 | 0 | 0 |
| | 6 | 10 | 0 | 50 | 0 | 40 | 100 | 0.01 | 0.02 |

Ex.: "Example", Comp. Ex.: "Comparative Example", Amt.; "Amount", pbw: "parts by weight"

TABLE 2

| | | SSA (m²/g) | Pore Diam. (nm) | Pore Vol. (ml/g) | Eval. of Porosity | Water Absorption value (ml/100 g) | Oil Absorption value (ml/100 g) | Hydrophilicity | | Redispersibility in Ethanol | | Redispersibility in Water | |
|---|---|---|---|---|---|---|---|---|---|---|---|---|---|
| | | | | | | | | Precipitation Time | Eval. | Num. of Shakes | Eval. | Num. of Shakes | Eval. |
| Ex. | 1 | 65.2 | 8.1 | 0.19 | P | 144 | 131 | 7 hs. | S | 10 | A | 73 | A |
| | 2 | 61.7 | 10.8 | 0.05 | P | 158 | 127 | 2 hs. | VH | 8 | A | 32 | A |
| | 3 | 4.9 | 14.6 | 0.02 | P | 165 | 110 | 1 hs. 20 min. | VH | 6 | A | 26 | A |
| | 4 | 90.4 | 11.0 | 0.33 | P | 190 | 157 | 20 min. | VH | 2 | A | 1 | A |
| | 5 | 43.0 | 5.5 | 0.14 | P | 217 | 143 | 15 min. | VH | 27 | A | 50 | A |
| | 6 | 9.5 | 4.7 | 0.04 | P | 197 | 105 | 20 min. | VH | 58 | A | 41 | A |
| | 7 | 78.6 | 9.3 | 0.27 | P | 174 | 194 | 20 min. | VH | 2 | A | 2 | A |
| | 8 | 79.5 | 9.9 | 0.28 | P | 201 | 151 | 5 hs. | S | 1 | A | 4 | A |
| | 9 | 184.0 | 9.5 | 0.51 | P | 320 | 306 | 2 hs. | VH | 1 | A | 1 | A |
| Comp. Ex. | 1 | 85.2 | 11.3 | 0.30 | P | 142 | | *1 | VPH | 24 | A | — | — |
| | 2 | 78.8 | 12.6 | 0.24 | P | 125 | 140 | 12 hs. | PH | 20 | A | 120 | NA |
| | 3 | —*2 | — | — | — | — | — | — | — | — | — | — | — |
| | 4 | — | — | — | — | — | — | — | — | — | — | — | — |
| | 5 | 0.7 | — | — | NP | 112 | 75 | 90 min. | VH | 130 | NA | 25 | A |
| | 6 | — | — | — | — | — | — | — | — | — | — | — | — |

*1: No precipitation even after 48 hours
*2: No measurement or evaluation performed
Ex.: "Example", Comp. Ex.: "Comparative Example", SSA: "Specific Surface Area", Pore Diam.: "Pore Diameter", Pore Vol.: "Pore Volume", Eval.: "Evaluation", Num. of Shakes: "Number of Shakes", P: "Porous", NP: "Not porous", VH: "Very hydrophilic", S: "Sufficiently hydrophilic", PH: "Poorly hydrophilic", VPH: "Very poorly hydrophilic", A: "Acceptable", NA: "Not acceptable"

As could be understood from the results shown in Table 1 and Table 2, the resin particles of examples 1 to 9 are porous and superior in all of water absorbance, oil absorbance, hydrophilicity, redispersibility in ethanol, and redispersibility in water.

Specifically, the resin particles of examples 1 to 9 are porous particles with a specific surface area of 4.9 m²/g to 184 m²/g, exhibit both high water absorption value and high oil absorption value, and have both superior water absorbance and superior oil absorbance, when compared with the resin particles of comparative example 5 which are non-porous particles with a specific surface area of 0.7 m²/g.

The resin particles of examples 1 to 9 obtained from polymerization of a monomer mixture containing 3 wt % to 40 wt % (specifically, 5 wt % to 30 wt %) mono(meth) acrylate-based monomer are superior in hydrophilicity and water absorbance when compared with the resin particles of comparative examples 1 to 2 obtained from polymerization of a monomer mixture containing less than 3 wt % mono (meth)acrylate-based monomer.

Figure 2:
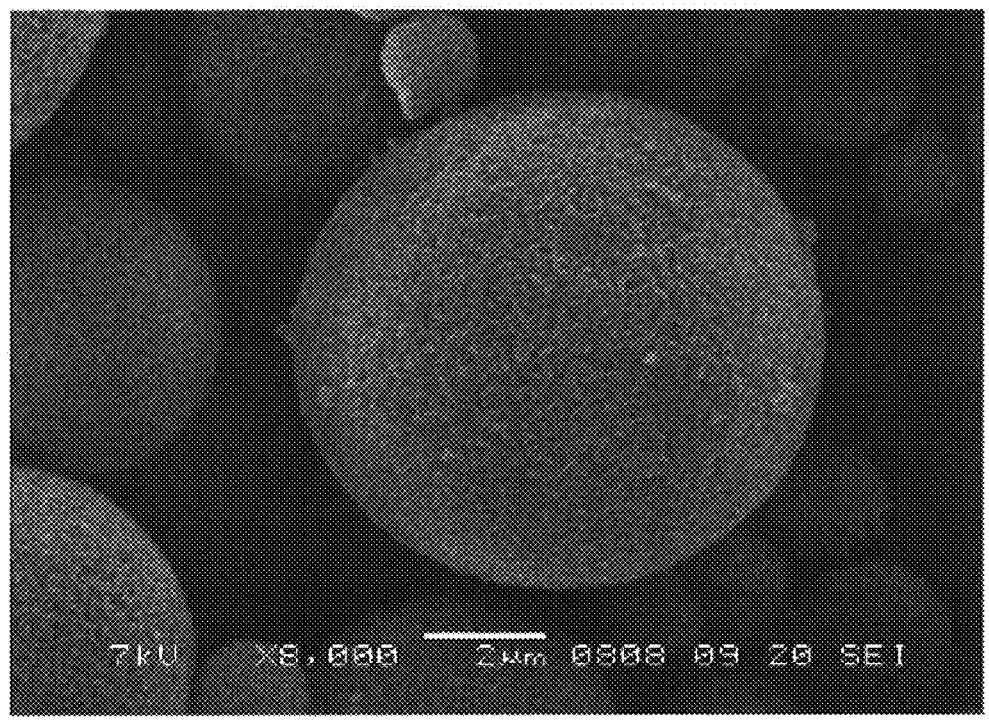
FIG. 2 is a scanning electron microscope (SEM) image of porous resin particles in accordance with example 7 of the present invention.
Figure 3:
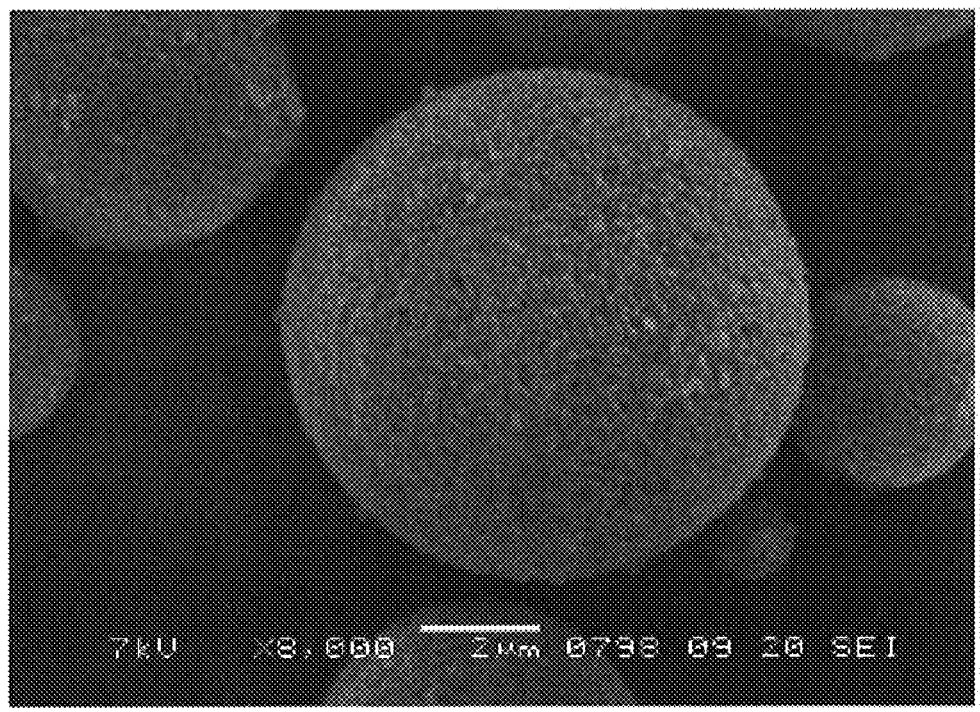
FIG. 3 is a scanning electron microscope (SEM) image of porous resin particles in accordance with example 8 of the present invention.

After the water absorption values of the resin particles of examples 1 to 9 were measured, the resin particles were dried to evaporate their water content. The resin particles were observed with an enlarger projector and turned out to have remained spherical as shown in FIGS. 1 to 3. The resin particles of examples 1 to 9 were hence spherical porous resin particles. If they are blended in cosmetic materials and other external preparations, they exhibit improved spreading and slippage when the external preparation is applied to the skin. They also move into the skin where the external preparation is applied, and scatter light in various directions, which covers up spots, freckles, and pores. Since the resin particles of examples 1 to 9 are spherical porous resin particles, if they are blended in a coating material, they exhibit improved slippage when the coating material is applied to a base material. They also scatter the light that travels through the coating film on the base material and reflects off the base material. Furthermore, since the resin particles of examples 1 to 9 are spherical porous resin particles, if they are blended in a light diffusion member, they scatter the light that reflects off the light diffusion member.

Example 10

Example of Body Lotion Manufacturing

The resin particles (porous resin particles) obtained in example 4 (3 parts by weight), 50 parts by weight of ethanol as a dispersion medium, 0.1 parts by weight of glycyrrhizic acid as an anti-inflammatory agent, 46.4 parts by weight of purified water as a dispersion medium, and 0.5 parts by weight of fragrance were mixed thoroughly in a mixer to obtain a body lotion as an external preparation.

The obtained body lotion exhibited superior slippage when applied to the skin, was smooth, and gave excellent feel when used. The precipitated resin particles were readily redispersed by merely lightly shaking the body lotion before use, which made the body lotion easy to use. Furthermore, the body lotion was so superior in water absorbance and oil absorbance that it could absorb sweat and sebum and keep the skin smooth and silky when applied to the skin.

Example 11

Example of Pre-Shave Lotion Manufacturing

The resin particles (porous resin particles) obtained in example 4 (4 parts by weight), 91 parts by weight of ethanol as a dispersion medium, 5.0 parts by weight of 1,3-butylene glycol as a dispersion medium, 2.0 parts by weight of ethyl hexanoate cetyl, and a suitable amount of fragrance were mixed thoroughly in a mixer to obtain a pre-shave lotion as an external preparation.

The obtained pre-shave lotion exhibited superior slippage when applied to the skin, was smooth, and gave excellent feel when used. The resin particles were readily redispersed by merely lightly shaking the pre-shave lotion before use, which made the pre-shave lotion easy to use. Furthermore, the pre-shave lotion was so superior in water absorbance and oil absorbance that it could absorb sweat and sebum and keep the skin smooth and silky when applied to the skin.

Example 12

Example of Powder Foundation Manufacturing

The resin particles (porous resin particles) obtained in example 4 (15 parts by weight), 21 parts by weight of sericite as a clay mineral, 51 parts by weight of white mica as a clay mineral, 0.6 parts by weight of red iron oxide as a color ingredient, 1 part by weight of yellow iron oxide as a color ingredient, and 0.1 parts by weight black iron oxide as a color ingredient were mixed using a Henschel mixer to obtain a mixture. Next, to this mixture was added a mixture obtained by mixing and dissolving 10 parts by weight of 2-ethyl hexanoate cetyl, 1 part by weight of sorbitan sesquioleate, and 0.2 parts by weight of a preservative. The entire mixture was uniformly mixed. A fragrance (0.1 parts by weight) was further added to the obtained mixture and mixed. After that, the mixture was pulverized and sieved. The pulverized and sieved article was compression molded into a metal plate to obtain a powder foundation.

The obtained powder foundation exhibited superior slippage when applied to the skin, was smooth, and gave excellent feel when used. The powder foundation was so superior in water absorbance and oil absorbance that it could absorb sweat and sebum and keep the skin smooth and silky when applied to the skin. The powder foundation also fixed skin flaws (covered up spots, freckles, pores, etc.) when applied to the skin.

Example 13

Example of Emulsion Foundation Manufacturing

The resin particles (porous resin particles) obtained in example 4 (20.0 parts by weight), 6.0 parts by weight of sericite as a clay mineral, 3.0 parts by weight of titanium dioxide, and a suitable amount of pigment were mixed in a kneader to prepare a powder article.

Separately from the powder article, 5.0 parts by weight of polyethylene glycol (polyethylene glycol 4000), 1.0 part by weight of triethanolamine as a pH-adjuster, 5.0 parts by weight of propylene glycol, and 0.5 parts by weight of VEEGUM®, manufactured by Vanderbilt as a clay mineral were added to 50.2 parts by weight of purified water and heated so that they could dissolve. The previously prepared powder article was added to the obtained solution. After the powder was uniformly dispersed using a homomixer, the mixture was maintained at 70° C. to obtain an aqueous phase component.

Next, separately from the aqueous phase component, 2.0 parts by weight of stearic acid, 0.3 parts by weight of cetyl alcohol, 20.0 parts by weight of liquid paraffin, a suitable amount of fragrance, and a suitable amount of preservative were mixed and heated so that they could dissolve. After that, the mixture was maintained at 70° C. to obtain an oil phase component.

The aqueous phase component was added to the obtained oil phase component. The mixture was subjected to preliminary emulsification, and uniformly emulsified and dispersed using a homomixer. After that, the mixture was cooled down while stirring to obtain an emulsion foundation.

The obtained emulsion foundation exhibited superior slippage when applied to the skin, was smooth, and gave excellent feel when used. The powder foundation was so superior in water absorbance and oil absorbance that it could absorb sweat and sebum and keep the skin smooth and silky when applied to the skin. The emulsion foundation also fixed skin flaws (covered up spots, freckles, pores, etc.) when applied to the skin.

Example 14

Example of Loose Powder Manufacturing

The resin particles (porous resin particles) obtained in example 4 (21.0 parts by weight), 30.0 parts by weight of mica as a clay mineral, 30.0 parts by weight of sericite as a clay mineral, 9.0 parts by weight titanium sericite as a clay mineral, 8.0 parts by weight of titanium dioxide, and 2.0 parts by weight of iron oxide as a color ingredient were mixed using a Henschel mixer. After that, the mixture was pulverized once with a rotor speed mill ZM-100 manufactured by Retsch (a 12-blade rotor was used with a 1-mm screen being attached and at a rotational speed of 14000 rpm) to obtain loose powder.

The obtained loose powder exhibited superior slippage when applied to the skin, was smooth, and gave excellent feel when used. The loose powder, when applied to the skin, so swiftly absorbed sweat and sebum that it could provide excellent durability of makeup. The loose powder also fixed skin flaws (covered up spots, freckles, and pores, etc.).

Example 15

Example of Body Powder Manufacturing

The resin particles (porous resin particles) obtained in example 4 (50.0 parts by weight), 25.0 parts by weight of mica as a clay mineral, and 25.0 parts by weight of sericite as a clay mineral were mixed using a Henschel mixer. After that, the mixture was pulverized once with a rotor speed mill ZM-100 manufactured by Retsch (a 12-blade rotor was used with a 1-mm screen being attached and at a rotational speed of 14000 rpm) to obtain a body powder.

The obtained body powder exhibited superior slippage when applied to the skin and gave excellent feel when used. The body powder also swiftly absorbed sweat and sebum.

Example 16

Example of Coating Material Manufacturing

The resin particles (porous resin particles) obtained in example 4 (3 parts by weight) and 20 parts by weight of a commercially available aqueous solution of resin binder (solid content 30%, manufactured by ALBERDINGK, trade name "U330") were stirred for 3 minutes using a centrifugal stirrer to obtain a dispersion liquid. In this process, the resin particles were readily dispersed in the aqueous resin binder by stirring for 3 minutes using the centrifugal stirrer.

The obtained dispersion liquid was left to stand for 3 hours. After that, the dispersion liquid was stirred again for 3 minutes using the centrifugal stirrer to obtain a coating material.

The obtained coating material exhibited such superior redispersibility that the resin particles could be redispersed by simply shaking even after 12 hours had passed.

Coating of Acrylic Board

A 3-mm thick acrylic board was spray-coated with the coating material to prepare a 50 μm-thick matting coating film. The obtained coating film did not have any visible bumps (projections) and exhibited good matting properties.

Example 17

Example of Light Diffusion Member Manufacturing

A 1:1 toluene/methyl ethyl ketone mixed solution (6 parts by weight) was added to a dispersion liquid containing a mixture of 3 parts by weight of the resin particles (porous resin particles) obtained in example 4 and 4.5 parts by weight of an acrylate-based binder manufactured by Mitsubishi Rayon Co., Ltd. (trade name: "Dianal® LR-102"). The resultant mixture was stirred for 3 minutes using a centrifugal stirrer. The obtained solution was left to stand for 3 hours. After that, it was stirred again for 3 minutes using the centrifugal stirrer. Next, the obtained solution was applied onto a PET film using a 100 μm coater. A coating film was formed on the PET film by drying the obtained film for 1 hour in a drier that was maintained at 70° C., to obtain a light diffusion film as a light diffusion member.

The face to be coated of the obtained light diffusion film was reciprocally polished 20 times with a cloth using a fastness rubbing tester and after the polishing, visually observed for scratches on the light diffusion film. No line scratches or peeling of the resin particles were found, which confirmed that the resin particles were compatible with the acrylate-based binder in the coating film. The obtained light diffusion film also exhibited excellent light diffusibility because of the blended resin particles.

The present invention may be implemented in various forms without departing from its spirit and main features. Therefore, the aforementioned examples are for illustrative purposes only in every respect and should not be subjected to any restrictive interpretations. The scope of the present invention is defined only by the claims and never bound by the specification. Those modifications and variations that may lead to equivalents of claimed elements are all included within the scope of the invention.

The present application hereby claims priority on Japanese Patent Application, Tokugan, No. 2012-018302 filed Jan. 31, 2012 in Japan, the entire contents of which are hereby incorporated herein by reference.

The invention claimed is:

1. Porous resin particles of a polymer of a monomer mixture,
   said monomer mixture comprising:
   a mono(meth)acrylate-based monomer in an amount of 3 wt % to 40 wt % containing: an ethylenic unsaturated group only in a (meth)acrylic acid residue, and a hydroxyl group and at least either an ether group or an ester group in an alcohol residue;
   another monofunctional vinyl-based monomer in an amount of 10 wt % to 69 wt % containing a single ethylenic unsaturated group; and
   a polyfunctional vinyl-based monomer in an amount of 30 wt % to 70 wt % containing two or more ethylenic unsaturated groups,
   wherein the porous resin particles have a water absorption value of 140 ml to 400 ml per 100 g of said particles, and an oil absorption value of 100 ml to 400 ml per 100 g of said particles.

2. The porous resin particles as set forth in claim 1, wherein said porous resin particles have pore diameter of from 4 nm to 20 nm.

3. The porous resin particles as set forth in claim 1 wherein the mono(meth)acrylate-based monomer is a compound of either general formula (1) or general formula (2):

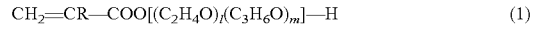

$$CH_2=CR-COO[(C_2H_4O)_l(C_3H_6O)_m]-H \quad (1)$$

where R is either H or $CH_3$, l is from 0 to 50, m is from 0 to 50, and l+m>1, and

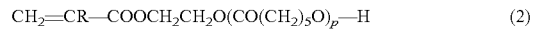

$$CH_2=CR-COOCH_2CH_2O(CO(CH_2)_5O)_p-H \quad (2)$$

where R is either H or $CH_3$, and p is from 1 to 50.

4. The porous resin particles as set forth in claim 1, wherein the another monofunctional vinyl-based monomer is an alkyl(meth)acrylate-based monomer.

5. The porous resin particles as set forth in claim 1, wherein the polyfunctional vinyl-based monomer is a polyfunctional (meth)acrylate-based monomer containing two or more ethylenic unsaturated groups.

6. Porous resin particles of a polymer of a monomer mixture,
   said monomer mixture comprising:
   a mono(meth)acrylate-based monomer in an amount of 3 wt % to 40 wt % containing: an ethylenic unsaturated group only in a (meth)acrylic acid residue, and a hydroxyl group and at least either an ether group or an ester group in an alcohol residue;

another monofunctional vinyl-based monomer containing a single ethylenic unsaturated group; and a polyfunctional vinyl-based monomer containing two or more ethylenic unsaturated groups, wherein the porous resin particles have a water absorption value of 140 ml to 400 ml per 100 g of said particles, an oil absorption value of 100 ml to 400 ml per 100 g of said particles, and a pore diameter of 4 nm to 20 nm.

7. The porous resin particles as set forth in claim 1, wherein said porous resin particles have a specific surface area of 3 $m^2$/g to 300 $m^2$/g.

8. A method for manufacturing the porous resin particles having a water absorption value of 140 ml to 400 ml per 100 g of said particles, and an oil absorption value of 100 ml to 400 ml per 100 g of said particles according to claim 1, said method comprising the step of suspension-polymerizing a monomer mixture in the presence of a non-polymerizable organic solvent as a pore-forming agent, an anionic surfactant, and a zwitterionic surfactant, wherein said monomer mixture comprises: a mono(meth)acrylate-based monomer in an amount of 3 wt % to 40 wt % containing: an ethylenic unsaturated group only in a (meth)acrylic acid residue, and a hydroxyl group and at least either an ether group or an ester group in an alcohol residue; another monofunctional vinyl-based monomer in an amount of 10 wt % to 69 wt % containing a single ethylenic unsaturated group; and a polyfunctional vinyl-based monomer in an amount of 30 wt % to 70 wt % containing two or more ethylenic unsaturated groups, wherein in said step, the pore-forming agent is used in an amount from 50 parts by weight to 300 parts by weight per 100 parts by weight of the monomer mixture.

9. The method for manufacturing porous resin particles as set forth in claim 8, wherein the pore-forming agent is an acetate ester.

10. A dispersion liquid, comprising: the porous resin particles as set forth in claim 1; and at least one dispersion medium selected from the group consisting of water and alcohol.

11. An external preparation, comprising the porous resin particles as set forth in claim 1.

12. The external preparation as set forth in claim 11, wherein said external preparation is a powdery cosmetic material.

13. A coating material, comprising the porous resin particles as set forth in claim 1.

14. A light diffusion member, comprising the porous resin particles as set forth in claim 1.

15. A dispersion liquid, comprising: the porous resin particles as set forth in claim 6; and at least one dispersion medium selected from the group consisting of water and alcohol.

16. An external preparation, comprising the porous resin particles as set forth in claim 6.

17. The external preparation as set forth in claim 16, wherein said external preparation is a powdery cosmetic material.

18. A coating material, comprising the porous resin particles as set forth in claim 6.

19. A light diffusion member, comprising the porous resin particles as set forth in claim 6.

* * * * *